US008048210B2

(12) United States Patent
Dallas et al.

(10) Patent No.: US 8,048,210 B2
(45) Date of Patent: Nov. 1, 2011

(54) WEB COMPRISING FINE FIBER AND REACTIVE, ADSORPTIVE OR ABSORPTIVE PARTICULATE

(75) Inventors: Andrew J. Dallas, Apple Valley, MN (US); Lefei Ding, St. Paul, MN (US); Jon D. Joriman, Little Canada, MN (US); Dustin Zastera, St. Paul, MN (US); James R. Giertz, Eden Prairie, MN (US); Veli Kalayci, Farmington, MN (US); Hoo Y. Chung, Edina, MN (US)

(73) Assignee: Donaldson Company, Inc., Minneapolis, MN (US)

( * ) Notice: Subject to any disclaimer, the term of this patent is extended or adjusted under 35 U.S.C. 154(b) by 147 days.

(21) Appl. No.: 12/648,772

(22) Filed: Dec. 29, 2009

(65) Prior Publication Data
US 2010/0176068 A1 Jul. 15, 2010

Related U.S. Application Data

(62) Division of application No. 11/707,761, filed on Feb. 13, 2007, now Pat. No. 7,655,070.

(60) Provisional application No. 60/773,067, filed on Feb. 13, 2006.

(51) Int. Cl.
*B01D 59/26* (2006.01)
(52) U.S. Cl. ........... 96/154; 96/134; 96/135; 96/153; 210/502.1; 442/340; 428/221; 428/357
(58) Field of Classification Search .......... 96/134, 96/135, 153, 154; 210/502.1; 442/340; 428/221, 428/357
See application file for complete search history.

(56) References Cited

U.S. PATENT DOCUMENTS

| 3,019,127 | A | 1/1962 | Czerwonka et al. |
| 3,034,947 | A | 5/1962 | Conlisk et al. |
| 3,676,242 | A | 7/1972 | Prentice |
| 3,826,067 | A | 7/1974 | Wilder et al. |
| 3,841,953 | A | 10/1974 | Lohkamp et al. |
| 3,849,241 | A | 11/1974 | Butin et al. |
| 3,878,014 | A | 4/1975 | Melead |
| 3,900,648 | A | 8/1975 | Smith |

(Continued)

FOREIGN PATENT DOCUMENTS

DE   20 2005 020 566   5/2006

(Continued)

OTHER PUBLICATIONS

Frautmann, P. et al., "High Performance Nanofibre Coated Filter Media for Engine Intake Air Filtration," *Filtration*, vol. 6, No. 1, pp. 53-56 (2006).

(Continued)

*Primary Examiner* — Robert J Hill, Jr.
*Assistant Examiner* — Christopher P Jones
(74) *Attorney, Agent, or Firm* — Pauly, DeVries, Smith & Deffner, L.L.C.

(57) ABSTRACT

The assemblies of the invention can comprise a fine fiber layer having dispersed within the fine fiber layer an active particulate material. Fluid that flows through the assemblies of the invention can have any material dispersed or dissolved in the fluid react with, be absorbed by, or adsorbed onto, the active particulate within the nanofiber layer. The structures of the invention can act simply as reactive, absorptive, or adsorptive layers with no filtration properties, or the structures of the invention can be assembled into filters that can filter particulate from a mobile fluid while simultaneously reacting, absorbing, or adsorbing materials from the mobile fluid.

28 Claims, 7 Drawing Sheets

U.S. PATENT DOCUMENTS

| | | | |
|---|---|---|---|
| 3,971,373 | A | 7/1976 | Braun |
| 4,100,324 | A | 7/1978 | Anderson et al. |
| 4,227,904 | A | 10/1980 | Kasmark, Jr. |
| 4,429,001 | A | 1/1984 | Kolpin et al. |
| 4,460,642 | A | 7/1984 | Errede et al. |
| 4,650,506 | A | 3/1987 | Barris et al. |
| 4,753,730 | A | 6/1988 | Maurer |
| 4,765,812 | A | 8/1988 | Homonoff et al. |
| 4,868,032 | A | 9/1989 | Eian et al. |
| 4,910,064 | A | 3/1990 | Sabee |
| 5,082,476 | A | 1/1992 | Kahlbaugh et al. |
| 5,135,792 | A | 8/1992 | Hogan |
| 5,223,139 | A | 6/1993 | Ruger et al. |
| 5,238,474 | A | 8/1993 | Kahlbaugh et al. |
| 5,328,758 | A | 7/1994 | Markell et al. |
| 5,332,426 | A | 7/1994 | Tang et al. |
| 5,342,418 | A | 8/1994 | Jesse |
| 5,344,698 | A | 9/1994 | Rock et al. |
| 5,350,443 | A | 9/1994 | Von Blucher et al. |
| 5,364,456 | A | 11/1994 | Kahlbaugh et al. |
| 5,423,892 | A | 6/1995 | Kahlbaugh et al. |
| 5,468,536 | A | 11/1995 | Whitcomb et al. |
| 5,478,466 | A | 12/1995 | Heilmann et al. |
| 5,486,410 | A | 1/1996 | Groeger et al. |
| 5,607,490 | A | 3/1997 | Taniguchi et al. |
| 5,614,283 | A | 3/1997 | Potnis et al. |
| 5,626,820 | A | 5/1997 | Kinkead et al. |
| 5,638,569 | A | 6/1997 | Newell |
| 5,652,048 | A | 7/1997 | Haynes et al. |
| 5,662,728 | A | 9/1997 | Groeger |
| 5,672,399 | A | 9/1997 | Kahlbaugh et al. |
| 5,681,469 | A | 10/1997 | Barboza et al. |
| 5,779,847 | A | 7/1998 | Groeger |
| 5,800,706 | A | 9/1998 | Fischer |
| 5,885,696 | A | 3/1999 | Groeger |
| 5,952,092 | A | 9/1999 | Groeger et al. |
| 5,965,091 | A | 10/1999 | Navarre et al. |
| 5,972,808 | A | 10/1999 | Groeger et al. |
| 5,993,905 | A | 11/1999 | Sheehan |
| 6,165,572 | A | 12/2000 | Kahlbaugh et al. |
| 6,331,351 | B1 | 12/2001 | Waters et al. |
| 6,371,977 | B1 | 4/2002 | Bumbarger et al. |
| 6,492,183 | B1 | 12/2002 | Perman et al. |
| 6,514,306 | B1 | 2/2003 | Rohrbach et al. |
| 6,554,881 | B1 | 4/2003 | Healey |
| 6,646,179 | B1 | 11/2003 | Melius et al. |
| 6,673,136 | B2 | 1/2004 | Gillingham et al. |
| 6,743,273 | B2 | 6/2004 | Chung et al. |
| 7,033,493 | B2 | 4/2006 | McGarvey et al. |
| 7,163,349 | B2 | 1/2007 | Policicchio et al. |
| 7,182,537 | B2 | 2/2007 | Policicchio et al. |
| 7,501,013 | B2 | 3/2009 | Oda |
| 7,655,070 | B1 | 2/2010 | Dallas et al. |
| 2003/0099576 | A1 | 5/2003 | Li et al. |
| 2003/0106294 | A1 | 6/2003 | Chung et al. |
| 2003/0211069 | A1 | 11/2003 | Deckner et al. |
| 2004/0116025 | A1 | 6/2004 | Gogins et al. |
| 2005/0215965 | A1 | 9/2005 | Schmidt et al. |
| 2005/0266760 | A1 | 12/2005 | Chhabra et al. |
| 2006/0004336 | A1 | 1/2006 | Zhang et al. |
| 2006/0246798 | A1 | 11/2006 | Reneker et al. |
| 2007/0021569 | A1 | 1/2007 | Willis et al. |
| 2007/0062855 | A1 | 3/2007 | Chase et al. |
| 2007/0210008 | A1 | 9/2007 | Sprenger et al. |
| 2008/0083369 | A1 | 4/2008 | Nakamura et al. |
| 2008/0272520 | A1 | 11/2008 | Komura et al. |

FOREIGN PATENT DOCUMENTS

| | | |
|---|---|---|
| JP | 7-265640 | 10/1995 |
| JP | 10-165731 | 6/1998 |
| WO | WO 03/013732 | 2/2003 |
| WO | WO 03/080905 A1 | 10/2003 |
| WO | WO 2005/005696 A1 | 1/2005 |
| WO | WO 2005/005704 A2 | 1/2005 |
| WO | WO 2006/049664 A1 | 5/2006 |
| WO | WO 2006/084106 A1 | 8/2006 |
| WO | WO 2007/016970 A1 | 2/2007 |
| WO | WO 2007/054039 A1 | 5/2007 |
| WO | WO 2007/054040 A2 | 5/2007 |
| WO | WO 2007/092303 A2 | 8/2007 |

OTHER PUBLICATIONS

Hansen, L. et al., "Water Absorption and Mechanical Properties of Electrospun Structured Hydrogels," *Journal of Applied Polymer Science*, vol. 95, pp. 427-434 (2005).

Ko, F. et al., "Electrospinning of Continuous Carbon Nanotube-Filled Nanofiber Yarns," *Adv. Mater*. vol. 15, No. 14, pp. 1161-1165 (Jul. 17, 2003).

Velcon Filters, Inc. Service Bulletin, May 2007 "Migration of Superabsorbent Polymer (SAP) Media Downstream of Filtration" http://www.velcon.com/doc/Vol6-No1-05.21.07.pdf.

European Office Action dated Aug. 17, 2010 for European Patent Application No. 07750930.5, filed Feb. 13, 2007 (4 pages).

File History for co-pending U.S. Appl. No. 11/707,761, filed Feb. 13, 2007, now U.S. Patent No. 7,655,070 which issued on Feb. 2, 2010, entitled "Web Comprising Fine Fiber and Reactive Adsorptive or Absorptive Particulate" (268 pages).

Chinese Office Action mailed Jan. 13, 2011 in co-pending Chinese Patent Application 2007800133143 (13 pages).

Japanese Office Action mailed Dec. 20, 2010 in co-pending Japanese Patent Application No. 2008-554447 (8 pages).

WEB COMPRISING FINE FIBER AND REACTIVE, ADSORPTIVE OR ABSORPTIVE PARTICULATE

CROSS-REFERENCE TO RELATED APPLICATION

This application is a divisional application of U.S. application Ser. No. 11/707,761, filed Feb. 13, 2007, which application claims benefit of U.S. Provisional Patent Application Ser. No. 60/773,067, filed Feb. 13, 2006, which applications are hereby incorporated herein it its entirety.

FIELD OF THE INVENTION

The invention relates to a web or fiber structure. The filter, element or medium structures of the invention can act as a reactive, adsorptive or absorptive layer or in a filtration mode. The structure comprises a collection fiber and a reactive, adsorptive or absorptive particulate that also acts as an active particulate, active material fiber, spacer or separation means. The particulate can act as an absorbent, adsorbent or reactant.

BACKGROUND OF THE INVENTION

Polymer webs can be made by extrusion, melt spinning, air laid and wet laid processing, etc. The manufacturing technology of filter structures is vast for obtaining structures that can separate the particulate load from a mobile fluid stream. Such filtration media include surface loading media and depth media in which these media can be produced in a variety of geometric structures. Principles relating to the use of such media are described in Kahlbaugh et al., U.S. Pat. Nos. 5,082,476; 5,238,474; 5,364,456 and 5,672,399. In any filter structure containing any arbitrarily selected filtration medium, the filter must remove a defined particle size, and at the same time, have sufficient lifetime to be economically justifiable in its particulate removing properties. Lifetime is generally considered to be the time between installation and the time a filter obtains sufficient particulate load such that the pressure drop across the filter is greater than a predetermined level. An increased pressure drop can cause filter bypass, mechanical filter failure, fluid starvation, or other operating problems. Filtration efficiency is the characteristic of the filtration media that is related to the fraction of the particulate removed from the mobile stream. Efficiency is typically measured by a set test protocol defined below.

Surface loading filter media often comprise dense mats of fiber having a non-woven structure that is placed across the path of a mobile fluid stream. While the mobile fluid stream passes through the structure of the formed non-woven fibers, the particulate is typically removed from the stream at the filter surface with a certain efficiency and remains on the surface. In contrast to surface loading structures, depth media typically include a relatively (compared to surface loading media) thick structure of fiber having a defined solidity, porosity, layer thickness and efficiency. Depth media and in particular, gradient density depth media are shown in Kahlbaugh et al., U.S. Pat. Nos. 5,082,476; 5,238,474 and 5,364,456. In general, depth media act in filtration operations by impeding the particulate loading in a mobile fluid stream within the filter layer. As the particulates impinge the depth media fibrous structure, the particulate remains within the depth media and is typically distributed onto and held with internal fibers and throughout the filter volume. In contrast, surface loading media typically accumulate particulate in a surface layer.

Groeger et al., U.S. Pat. No. 5,486,410, teach a fibrous structure typically made from a bicomponent, core/shell fiber, containing a particulate material. The particulate comprising an immobilized functional material held in the fiber structure. The functional material is designed to interact with and modify the fluid stream. Typical materials include silica, zeolite, alumina, molecular sieves, etc. that can either react with, or absorb materials, in the fluid stream. Markell et al., U.S. Pat. No. 5,328,758, use a melt blown thermoplastic web and a sorbative material in the web for separation processing. Errede et al., U.S. Pat. No. 4,460,642, teach a composite sheet of PTFE that is water swellable and contains hydrophilic absorptive particles. This sheet is useful as a wound dressing, as a material for absorbing and removing non-aqueous solvents, or as a separation chromatographic material. Kolpin et al., U.S. Pat. No. 4,429,001, teach a sorbent sheet comprising a melt blown fiber containing super absorbent polymer particles. Deodorizing or air purifying filters are shown in, for example, Mitsutoshi et al., JP 7265640 and Eiichiro et al., JP 10165731.

Many mobile fluid phases, including both gas and liquid phases, contain undesirable components suspended, dissolved, or otherwise entrained within the mobile phase. Such undesirable components may be chemically reactive or may be absorbable or adsorbable through the use of absorbents or adsorbents. Often these species form a phase that is fully miscible in the fluid and cannot be filtered, but can be removed only by chemical reaction absorbents or adsorbents. Examples of such materials are acidic or basic reacting compounds. Acid compounds include hydrogen sulfide, sulfur dioxide and other such species basic components include ammonia, amines, quaternary compounds and others. Further reactive gases such as $Cl_2$, $SO_2$, cyanide, phosgene and others can pose hazards. Lastly, a number of other compounds are objectionable due to odor, color or other undesirable properties. The removal of all such materials from a fluid phase, if possible, can be helpful in many end uses. The active layers of existing systems suffer from problems relating to the mechanical instability of the particulate in the layers. In many structures the particulate is not mechanically fixed in the layer and can be dislodged easily. In many structures, the amount of active materials available is limited by the nature of the substrate and the amounts of active material that can be loaded.

While both surface loading media and depth media have been used in the past and have obtained certain levels of performance, a substantial need remains in the industry for fluid phase treatment and filtration media that can provide new and different performance characteristics than formerly obtained. In particular, a need for improved efficiency, low-pressure drop and excellent adsorptive, absorptive, or reactive properties are needed in a structure with high activity and robust mechanical stability.

SUMMARY OF THE INVENTION

The web, filter, or other flow-through or flow-by structure of the invention can comprise a substantially continuous fine fiber mass or layer containing the particulate of the invention. A reactive, absorptive, or adsorptive fiber spacer or separation means in the form of a particle can be combined with, or otherwise dispersed in, the fiber mass. The web of the invention includes a fiber web or layer and a fiber separation means or fiber spacer means adhered to the fiber that can be used in the form of a reactive, absorbent, or adsorbent structure.

In one aspect, the web comprises a continuous fibrous structure with a continuous fiber phase and a reactive, absorptive, or adsorptive active particulate that can treat a fluid stream. The fluid stream can be a gas, or liquid with entrained materials. The entrained materials can be soluble or insoluble in the mobile fluids and can be particulates of either liquid or solid impurities. The liquids can be exemplified by aqueous solutions, nonaqueous fluids, water, oils, and mixtures thereof.

In a second aspect a similar structure can also act as a filter. The active particulate comprises a particulate phase dispersed with the fiber. The filter can be used to filter a mobile fluid such as a gaseous stream or a liquid stream. The filter can be used to remove impurities from the liquid stream or from the gaseous stream. Such impurities can be entrained particulates. The flow through and flow by structures can be used in structures that need no PTFE, stretched expanded Teflon® or other related porous fluoropolymer components for successful activity.

By dispersed, is meant that the active particulate is adhered to the fiber, held within a void space within the web or in a pocket penetrating partially into the web creating a space in the web surface. Once formed, the media comprising the fine fiber layer containing the active particulate of the invention can be combined with a media layer. That form can be used in a flow-by treatment unit or used in a flow-through filtration unit having adsorptive/absorptive or reactive properties. In a flow-by or pass-through unit, the media is simply configured in a form through which the mobile fluid can pass unimpeded by any filtration layer and simply contact the absorptive/adsorptive or reactive species formed in the fine fiber layer adjacent to the flow path of the fluid media. Alternatively, the fine fiber layer containing the active particulate and media can be formed in a flow-through filtration structure that can remove particulate from the mobile fluid while in the infiltration mode, the media of the invention can, in a filtration mode, remove the entrained particulate from mobile fluid and at the same time absorb, adsorb or chemically react with unwanted materials in the fluid phase that may or may not be in a particulate form.

The term filter refers to the structure that is actually used in treating a mobile fluid. A "filter" usually includes a housing with an inlet and outlet. The term "element" typically refers to a structure used in a filter assembly the includes a media layer and other parts resulting in a useful structurally stable unit that can be inserted and removed from the filter structure. Elements or webs of the invention include media layer that comprises a particulate dispersed throughout a fine fiber web. The combined fine fiber and particulate can be formed on a substrate layer to form a filter medium.

The particulate can comprise an amount of a single type of particulate or blend of dissimilar particles. For example, an active particulate can be blended with an inert particulate for use in such a layer. The inert particulate can comprise a single particulate or can be a blend of inert particulate that differs by composition particle size, particle morphology or some other particle aspect. Similarly, the active particulate can comprise a mixture of particulates including different active particulates. For example, a carbon particulate could be blended with a zeolite particulate. Alternatively, a carboxy methyl cellulose particulate can be blended with an ion exchange resin particulate in an active layer. Further, such active particulate can have a blended particulate in the sense that particulates of different size, shape or methodology can be combined in the active layers of the invention. The term "entrained particulate refers to impurities in the mobile fluid while the term "dispersed particulate" refers to the particulate deliberately included within the fiber layers of the invention.

The element of the invention can be used in one of two separate modes. These modes are designated as "flow-through" or "flow-by". In the flow-through mode, the mobile fluid, liquid or gas, passes through the fine fiber layer and substrate in a filtration mode in a flow substantially normal to the plane of the fiber layer. The entrained particulate can encounter and be removed by the element and as the fluid passes through the layers in contact with the particulate, the particulate can react with absorbed or adsorbed chemical materials suspended or dissolved in the fluid.

In the flow-by mode, the fluid path is generally parallel to the plane of the fine fiber layer or element surface. In the flow-by mode, the fluid contacts the surface of the layer and does not substantially flow through the element. While depending on viscosity, flow rate, temperature, element configuration, the fluid can to some degree penetrate the layer and can flow from layer to layer, the primary mode of transport of the fluid is bypassing the layer in a direction substantially parallel to the layer's surface. In such a mode, the liquid can contact the surface of the layer and chemical materials dissolved and suspended in the fluid can react with, be absorbed, or adsorbed by the particulate.

The flow-through and flow-by element can be used in a variety of formats. Flow-through element can be used in conventional filter structures including cartridge panel in some other filter structures, with the element in a pleated or unpleated mode. Similarly, the flow-by media can be included in the panel and cartridge structures.

One preferred mode of use of the flow-by material is in a rolled media. Rolled media are prepared by first forming the fine fiber and particulate layer by heat treating the fiber layer if needed and then rolling the element into a multi-layered roll having anywhere from 2 to 50 layers. The thickness of the roll, or a separation between the layers, determines the flow rate of fluid through the structure. The flow rates can be improved by introducing channels into the rolled media. Such channels can be preformed in the substrate upon which the fine fiber is spun, or the channels can be formed into the element after the fine fiber layer is formed on the substrate and then heat treated if necessary. Mechanical forms or spacers can be included with the processing steps. The forms or spacers can introduce the channel into the structure. At least one spacer portion can be included with the rolled material to inherently form a channel in one portion of the rolled structure. Further, additional spacers can be placed such that each layer of the rolled structure has at least one channel portion. An arbitrary number of spacers can be used. At least one spacer per layer can be used up to 5, 10 or 20 spacers per layer. After the spacer layers form a channel in the element, the spacers can be removed. The spacers can be removed in one mode by unrolling the element and physically removing the spacers from the element. However, in another mode, the spacers can be simply washed from the rolled assembly using a solvent in which the spacer (but not the substrate fine fiber or particulate) is soluble, thus removing the spacers and leaving flow-through channel structures. The spacers can be configured in virtually any shape or structure as long as the spacer can provide a channel from the first end of the roll to the second end of the roll providing a flow through path for fluid. Preferably the dimensions of the channel are greater than about 1 mm in major dimension and can range from about 1 to 500 mm in major dimension. The profile of the channels can be round, oval, circular, rectangular, square, triangular, or other cross-sectional profile. The profile can be regular, or it can be irregular and amorphous. Further along the channel, the cross-sectional profile of the channel can vary from one end to the other. For example, at the intake end of the rolled structure, the channel can have a relatively large cross-sectional area, whereas at the opposite end the cross-sectional area can be smaller than the input end. Additionally the input end can be smaller in cross-sectional area than the output end. Any other variation in size of the spacer can increase turbulence in the flow resulting in improved contact between the fluid and the particulate.

The filter or flow-through or flow-by structures of the invention are uniquely suited to provide useful properties. The flow-through structure can be used to absorb/adsorb or chemically react with mobile fluid phases that flow through the flow-through structures. The dispersed particulate within the flow-through structures can react with the mobile fluid (either liquid or gas), or absorb/adsorb, or react with intervening material within the fluid stream. The flow-through structures can act both as a filter, and as a structure that can react with, absorb, or adsorb materials in the fluid stream. Accordingly, the dual function flow-through structures can remove undesired particulate that is typically an insoluble phase in the fluid stream. In addition, the flow-through structures can also react with, absorb, or adsorb insoluble and soluble components of the fluid stream.

A particularly important fluid stream for the application includes air streams that can contain contaminates such as dust particulate, water, solvent residue, oil residue, mixed aqueous oil residue, harmful gases such as chlorine, benzene, sulfur dioxide, etc. Other typical liquid mobile phases include fuel, oils, solvents streams, etc. Such streams can be contacted with the flow-through structures of the invention to remove water, particulate contaminates, color-forming species, and minor amounts of soluble impurities. In many cases, the streams (both gaseous and liquid) can be contaminated by biological products including prions, viruses, bacteria, spores, DNA segments and other potentially harmful biological products or hazardous materials.

The active web or element of the invention can contain the fine fiber layer with the particulate dispersed within the fiber layer to absorb/adsorb or react with materials entrained in the mobile fluid phase. Such an element or web can be combined with other active or reactive species in a variety of forms. The particulate of the invention can be discrete particles separate from the fiber or the particulate can be adhered to or on the surface of the fiber. The particulate can be embedded into the fiber and can be partially or fully surrounded by the fiber mass. In order to form these structures, the particulate can be combined with the fiber after spinning, can be added to the fiber during spinning in the time the fiber dries and solidifies, or can be added to the spinning solution before spinning such that the particulate is embedded partially or fully in the fiber.

One method of forming an active layer can be by dispersing the active particulate in an aqueous or non-aqueous phase containing components, either forming the active particulate into a sheet layer, or adhering the active particulates to one or more of the components of the web or element of the invention. Any of the active particulates of the invention can be incorporated into either an aqueous or non-aqueous liquid phase for such purposes. In forming the non-aqueous material, a non-aqueous solvent, preferably a volatile solvent including such materials as lower alcohols, ethers, low boiling hydrocarbon fractions, chloroform methylene chloride, dimethyl sulfoxide (DMSO) and others, can be prepared by incorporating the active particulate of the material with soluble or dispersible binding materials. Such a solution can be applied to a fiber particulate sheet like substrate or other materials to form a layer containing the active particulates that can act in that form to absorb/adsorb or react with materials entrained in the mobile fluid phase. Alternatively, the active particulate of the invention can be dispersed in an aqueous solution or suspension of binding materials that can be similarly combined with, or coated on, fiber particulate or web sheet like substrates to form an active layer of active particulate. Alternatively, the active particulate of the invention can be dispersed or suspended in a mixed aqueous organic phase that combines an aqueous phase with organic phase. The organic phase can comprise additional solvents or other organic liquids or can comprise aqueous polymeric phase such as acrylic polymers, PTFE polymers. Such mixed phases can form layers containing the active particulate and additionally can contain cross-linking components that can form bonds between adjacent polymers, further curing the coatings of films.

A heat treatment or thermal bonding process can be used to form a distinct layer in which there is no fully distinct fiber. The heat treatment can heat the individual fibers to a temperature at or above a fusion or melting point of the individual fibers and then cause the fibers to adhere, coalesce, or form into a fused network, membrane or membrane-like structure. Depending on the temperature and pressure and time of the heat treatment, the heat treatment can convert the fibers from a randomly distributed layer of fiber of intermediate length having only surface contact into a layer where fibers are more intimately associated. At a minimum, the fiber is heated such that at the intersections of the fibers, the fibers fuse to form a fused network. With additional heat pressure, or time of heat treatment, the fibers can further melt and further coalesce into a more intimately associated web. With further temperature, time, and pressure, the fiber can more fully melt and spread into a porous membrane-like structure. The heat treatment also can alter the location of the particulate. In the instance that the fiber is simply distributed throughout, the particulate is distributed through the fine fiber. The heat treatment can fix the particulate into a structure in which the particulate is surface bonded to the heat treated fibrous, web, or membrane-like structure; however, depending again, on the temperature, time of heating, and pressure, the particulate can be incorporated into and throughout the porous membrane-like structure. Such a heat treated or calendared structure can have a layer of thickness that approximates that of the original fine fiber layer, or results in a layer that is thinner than the original fine fiber layer. Accordingly, if the original fine fiber layer has a thickness that ranges from about 0.5 to 200 microns, the resulting layer can have a thickness that ranges from about 0.5 to about 150 microns or smaller often up to 100 microns and sometimes up to 50 microns, depending on the amount of fiber spun, the particulate content and the degree of heat treatment, including heating, pressure, and time. One form of such a heat treatment process is the calendaring operation that can be used thermally. The calendaring process uses rollers, rollers and embossers, or embossers to form the heat treated layers. An embosser can be used with a bonding pattern that can result in a regular, intermediate, or random pattern. When a pattern is used, the pattern can occupy up to 50 percent of the surface area or more. Typically, the bonded array occupies about 1 to 75 percent of the surface area, often about 10-50 percent of the surface area.

Depending on the nature of the fine fiber used in the various layers and the rate of manufacture of the composites, the calendaring process parameters such as time, temperature, and pressure can be varied to achieve acceptable results. The temperature of the calendared rollers can range from about 25-200° C. The pressure exerted on the layers using the calendaring rollers or combination of rollers can range up to 500 psi and the speed of the composite through the heat treatment station can range from about 1 to about 500 feet per minute. The operating parameters of the heat treatment station must be adjusted such that the appropriate amount of heat is delivered to the fiber to obtain the correct ultimate structure. The heat cannot be so little as not to soften or melt some portion of the fiber and cannot be such that the fiber is simply melted and dispersed into the substrate. The total heat delivered can be readily adjusted to bond the fiber, soften the fiber overall or fully form the fibers into a porous membrane. Such minor adjustment of the operating parameters is well within the skill of the artisan.

The web or element of the invention can be comprised of a variety of different layers. Such layers can include both active and inactive layers. Active layers typically comprise a web of fine fiber with the particulates dispersed within the fine fiber or other impregnated layers or layers containing adsorbent/absorbent or reactive particulate or other such structures. Such layers can be formed into the useful element of the invention combined with protective layers, spatial layers, active layers, inactive layers, support layers, and all can be incorporated or encapsulated into conventional cartridge panel or other such protective structures. A preferred form of the active particulate comprises an adsorbent carbon particulate.

DETAILED DISCUSSION OF THE INVENTION

Figure 1A:
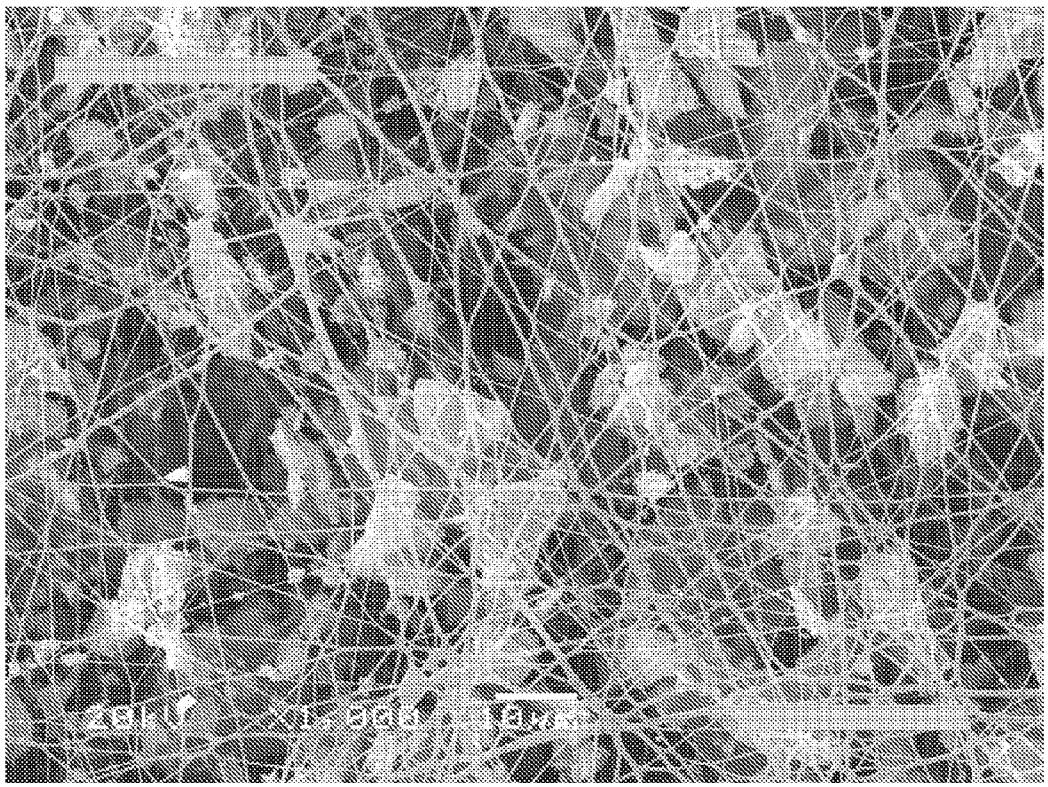
FIGS. 1A and 1B shows an end view of an element of the invention in which the element comprises layers of active media combined with layers of inactive media to provide a flow channel to regulate efficiency and activity.

The particulate materials of the invention have dimensions capable of improving the active properties and filtration properties of the media and layers of the invention. The materials can be made of a variety of useful materials that are inert, reactive, absorptive, or adsorptive. The materials can either be substantially inert to the mobile phase and entrained particulate load passing through the web or the materials can interact with the fluid, dissolved portions of the fluid or the particulate loading in the fluid. Some or all of the particulate can be inert. Preferred particulates are active, reactive, absorbent, or adsorbent materials. For the purpose of this invention, the term "inert" indicates that the material in the web does not either substantially chemically react with the fluid or particulate loading, or substantially physically absorb or adsorb a portion of the fluid or the particulate loading onto the particulate in any substantial quantity. In this "inert" mode, the particulate simply alters the physical parameters of the fiber layer and the media including one or more fiber layers. The active particulate of the invention can be added to any layer of the element of the invention using a variety of add on techniques. The particulate of the invention can be incorporated into the fine fiber layer during spinning of the fiber as discussed elsewhere in the application. In addition, the active particulate of the invention can be dissolved or dispersed into an aqueous or nonaqueous or mixed aqueous liquid and applied to any layer of a useful element of the invention.

When using an active particulate that interacts with the fluid or the particulate loading, the particulate can, in addition to altering the physical properties of the media or layers, react with or absorb or adsorb a portion of either the mobile fluid or the particulate loading for the purpose of altering the material that passes through the web. The primary focus of the technology disclosed herein is to improve the treatment properties of the layers to increase the reactivity/absorbent/adsorbent capacity or lifetime of the physical structure of the media or layers, and to improve filter performance where needed. In many such applications, a combination of an inert particle and an interactive particle will then be used.

The invention relates to polymeric compositions in the form of fine fiber such as microfibers, nanofibers, in the form of fiber webs, or fibrous mats used with a particulate in a unique improved filter structure. The web of the invention comprises a substantially continuous fiber phase and dispersed in the fiber mass a fiber separation means. In the various aspects of the invention, the fiber separation means can comprise a particulate phase in the web. The particulate can be found on the surface of the web, in surface products or throughout void spaces formed within the web. The fibrous phase of the web can be formed in a substantially singular continuous layer, can be contained in a variety of separate definable layers or can be formed into an amorphous mass of fiber having particulate inclusion phases throughout the web randomly forming inclusion spaces around the particulate and internal web surfaces. The particulate has a major dimension of less than about 5000 microns. For example, the particulate can have a major dimension of less than 200 microns, and can typically comprise about 0.05 to 100 microns or comprises about 0.1 to 70 microns. In the substantially continuous fine fiber layer, the layer has a layer thickness of about 0.0001 to 1 cm, 0.5 to 500 microns, about 1 to 250 microns, or about 2 to 200 microns. In the layer, dispersed in the fiber, is a means comprising a particulate with a particle size of about 0.25 to 200 microns, about 0.5 to 200 microns, about 1 to 200 microns about 10 to 200, or about 25 to 200 microns. The particulate is dispersed throughout the fiber in the layer. The particulate is present in an amount of about 0.1 to 50 vol %, about 0.5 to 50 vol %, about 1 to 50 vol %, about 5 to 50 vol % or about 10 to 50 vol %. The fiber has a diameter of about 0.001 to about 2 microns, 0.001 to about 1 micron, 0.001 to about 0.5 micron, or 0.001 to about 5 microns, and the layer having a fine fiber solidity of about 0.1 to 65%, about 0.5 to 50%; about 1 to 50%; about 1 to 30% and about 1 to 20%. The particulate is available in the layer in amount of about 1 to 1000 gm-m$^{-2}$, about 5 to 200 gm-m$^{-2}$ or about 10 to 100 gm-m$^{-2}$ of the layer.

The invention also relates to a membrane or membrane-like layer having a structure resulting from the polymeric material in the form of fine fiber. The membrane is formed by heat treating the fine fiber and the particulate to form a porous membrane. The membrane is a substantially continuous membrane or film-like layer having the particulate adhered to the surface of the membrane, imbedded into the membrane, or fully surrounded by the membrane polymer mass. In the membrane of the invention, the particulate can have a major dimension of less than 200 microns and typically has a dimension of about 0.05 to 100 microns or about 0.1 to 70 microns. The thickness of the membrane typically ranges from about 0.5 to about 5 microns having a pore size that ranges from about 0.1 to 5 microns often about 1 to 2 microns. The preferred membrane has a thickness of less than about 20 microns, has a pore size of about 0.5 to 3 microns. The particulate is present in the membrane structure in an amount of about 0.1 to 50 vol %. Lastly, in the membrane, the particulate is available in the membrane layer in an amount of up to about 10 kg-m$^{-2}$ typically about 0.1 to 1,000 gm-m$^{-2}$ about 0.5 to 200 gm-m$^{-2}$ or about 1 to 100 gm-m$^{-2}$ of the membrane.

The particulate can take a variety of regular geometric shapes or amorphous structures. Such shapes can include amorphous or random shapes, agglomerates, spheres, discs, ovals, extended ovals, cruciform shapes, rods, hollow rods or cylinders, bars, three dimensional cruciform shapes having multiple particulate forms extending into space, hollow spheres, non-regular shapes, cubes, solid prisms of a variety of faces, corners and internal volumes. The aspect ratio of the non-spherical particulate (the ratio of the least dimension of the particle to the major or largest dimension) of the invention can range from about 1:2 to about 1:10, preferably from about 1:2 to about 1:8.

The particulate of the invention can be made from both organic and inorganic materials and hybrid. The particulate that is non-interacting with the mobile fluid or entrained particulate phase comprises organic or inorganic materials. Organic particulates can be made from polystyrene or styrene copolymers expanded or otherwise, nylon or nylon copolymers, polyolefin polymers including polyethylene, polypropylene, ethylene, olefin copolymers, propylene olefin copolymers, acrylic polymers and copolymers including polymethylmethacrylate, and polyacrylonitrile. Further, the particulate can comprise cellulosic materials and cellulose derivative beads. Such beads can be manufactured from cellulose or from cellulose derivatives such as methyl cellulose, ethyl cellulose, hydroxymethyl cellulose, hydroxyethyl cellulose, and others. Further, the particulates can comprise a diatomaceous earth, zeolite, talc, clay, silicate, fused silicon dioxide, glass beads, ceramic beads, metal particulates, metal oxides, etc. Particulates intended for use in the present invention are characterized by average size in the range of from about 0.01 to 510 microns. Although submicron active particles are used, the present invention is applicable to fine particles up to 100 microns in average size. In any event, the average size of the active particles will be on the order of approximately 0.01 to 0.0001 of the average size of the particulates. Therefore, a relatively larger average size of the active particles requires a larger average size of the particulate. Particles include carbon particles such as activated carbon, ion exchange resins/beads, zeolite particles, diatomaceous earth, alumina particles such as activated alumina, polymeric particles including, for example, styrene monomer, and absorbent particles such as commercially available superabsorbent particles. Particularly suitable absorbent/adsorbent particles are low density, porous particles, and have pores and cavities including surface cavities, ranging in diameter from about the minimum for the pore size in carbon is 0.00035 microns, which is the carbon-carbon distance to 100 microns and interconnected by smaller pores. These pores and cavities beneficially provide inner surface for deposition, in particular monolayer deposition, of fine particles having an average size in the range of about 0.01 to 10 microns, and thereafter for accessibility to the immobilized fine particles. 1 cm$^3$ of these particles provides in bulk approximately 75 to 1,500 m$^2$ of available surface. Carbon particulates can be used in the form of filing divided activated carbon. Such activated carbons can be combined with other reactive adsorbent or adsorbent species that can be blended with, or adsorbed onto, the carbon surface. Other forms of active carbon can be used including carbon nanotubes, nanoparticles, nanowires, nanocarbon ropes or larger lattices or constructs in which the individual elements comprise a carbon nanotube. Such nanoparticles, such as buckyballs, smaller nanotubes (or nanotube portions thereof), nanoropes, etc. can be incorporated within the interior volume of the nanotube or incorporated into the carbon atom lattice of the nano structure. Additional atoms, molecules or components can add structure or function to the nano particulate material.

Small molecule, oligomeric and polymeric materials can be used in the invention. Small molecules typically have molecular weights of less than about 500, are typically made up of a single identifiable molecular unit and typically the units do not repeat in the molecular structure. Oligomer structures typically have somewhat larger molecular weights but typically have 2 to 10 repeating molecular units in a structure. Polymer units typically have substantially higher molecular weights and typically have substantially greater than 10 repeating units in a polymer structure. The differentiation between oligomeric and polymeric structures is not always clear cut; however, as the number of repeat units in the structure increases, the material tends to become more polymeric in nature.

The particulate can be mono-disperse or poly-disperse. In mono-disperse particulate, the majority of the particles are similar in diameter or the major dimension. For example, one example of a mono-disperse particulate has 80% to 90% of the particulate within about 0.8±0.5 microns or about 1±0.25 micron. In a poly-disperse material, the particulate has a substantial portion of particles with different diameters. A poly-disperse material could be a mixture of two mono-disperse materials or a material with a substantial amount of particulate material present throughout a broad range (e.g.) 0.1 to 10 or 0.01 to 100 microns.

The spheres or other shapes can be in a variety of different physical forms including solid and hollow form. The particulate can have a substantially spherical or slightly oval shaped spherical structure. The spheres can be solid or can have a substantial internal void volume. The shell thickness of the sphere can range from about 0.05 to about 500 microns while the sphere can range from about 0.5 to about 5000 microns. Other circular structures that can be used include simple toroidal structures, spiral or helical structures, or interlocking link type chain structures.

The particulate of the invention can also comprise a reactive absorbent or adsorbent fiber-like structure having a predetermined length and diameter. The aspect ratio of such a fiber is typically about 1 to about 10:1 having a fiber diameter that is typically larger in diameter than the fine fiber of the structure. The diameter ratio of the particulate fiber to the fine fiber is typically about 0.5 to about 5000:1. A variety of other regular shapes can be used including cylindrical, hollow cylindrical, cruciform structures, three-dimensional cruciform structures, I-beam structures, and others. The particulate can also be irregular in shape such that the particulate has a relatively well-defined major and minor dimension but has an exterior surface that is substantially irregular in nature. Many amorphous organic and inorganic particulates can have an irregular shape, but can have a size that can provide the spacing property of the particulate material. Depending upon the physical form and chemical nature of the spheres, the dimensions of the spheres can be manipulated by a secondary process such as super absorbency, solvent swelling, heat expansion, porosity changes, etc. Microspheres available from Expancel® can be heat-treated to expand the volume of the microspheres tremendously. Fine fiber and microsphere composite media can be produced according to this invention, and later upon a secondary treatment—not limited to heat— the structure of the composite media can be tuned in a controlled way, for example in the Expancel® case, depending upon the level of applied heat and temperature, one can control the degree of expansion of the microspheres. For example, by expanding the microspheres, the thickness and loftiness of the structure can be increased and thereby filtration properties can be altered in a desired way. It should be understood that such changes in the physical nature of the microsphere should be accommodated by the elasticity of the fine fiber as they would stretch in the case of expansion of the microspheres. Depending upon the reversibility of the change in microspheres, one can also create lofty structures and then collapse/shrink the structure to create dense/compact filtration structures.

The web can also be used in filtration applications as a surface media or depth media having a continuous web of fine fiber modified by the presence of a reactive, absorptive or adsorptive spacer or separation means in the form of a particulate that in combination with the fiber in the media, provides figure of merit, filtration efficiency, filtration permeability, depth loading and extended useful lifetime characterized by minimal pressure drop increase. The reactive, absorptive, or adsorptive spacer or separation means causes the fiber web to attain a structure, in which the fiber mass or web portion has reduced solidity, separated fibers or separated web portions within the structure, and increased depth of fiber layer, without increasing the amount of polymer or the number of fibers in the web. The reactive, adsorptive or absorptive, portion of the fiber web can react with reactive chemical species within a mobile fluid passing through the fiber layer or such chemical components of the mobile fluid can be absorbed or adsorbed by the absorptive or adsorptive portion of the fiber layer. The active particulate can be used with an inert particulate as long as the activity or activities of the particulate is maintained. The resulting structure obtains improved filtration properties in combination with resistance to increased pressure drop, improved (Figure of Merit,) improved permeability, improved efficiency, and the ability to remove both a particulate non-reactive load and a reactive gaseous or particulate load from a mobile fluid stream passing through the fiber layer. The fine fiber of the invention can be in the form of a structural fiber as discussed above. The fine fiber can be spun from a reactive fiber. Such reactive fibers can be made from polymers having reactive side chains such as amines, sulfonic acid, carboxylic acid, or other functional groups of side chains. Such side chains can be derived from the polymer itself. For example, a polyamine can be formed with a highly functional polyamine leaving acid and amine and mean functionality on the polymer side chains of substituents. Similarly, polysulfone or polyacrylic acid material can be formed having active or reactive acid groups. Similarly, ion exchange resin materials can be made having, within the resin particulate, acid, strongly acid, basic, or strongly basic functional groups that can add absorbent or reactive properties to the invention. Such materials can be dissolved or suspended and can be spun with the conventional fibers of the invention, or can be spun separately into the particle containing webs of the invention.

The web can be spun in such a way to disperse the active particulate or active separation means into the fiber. A preferred active particulate or spacer means comprises a reactive, absorptive or adsorptive particulate. Such particulate can be dispersed within the polymer containing solution. The particulate can be added to the web during formation or can be added after formation. Such a web, when electrospun, is characterized by a mass of interconnected nanofiber or fine fiber with the active separation or spacer means or particulate dispersed within the fiber web on the surface of the fiber web. Within the fiber web, the spacer particulate creates void spaces within the interconnected fibrous structure that reduces solidity and increases mobile fluid flow. The invention also comprises a web formed by forming a fine fiber mass with the simultaneous addition or a post spinning addition of the spacer particulate to the fiber layer. In such an embodiment, the particulate is interspersed throughout the mass of fibrous material. Lastly, the invention involves forming the spun layer in a complete finished web or thickness and then adding the active particulate to the surface of the web prior to incorporating the web into a useful article. Subsequent processing including lamination, calendaring, compression or other processes can incorporate the particulate into and through the fiber web. One advantage of either simultaneous addition of the particulate to the web as it is formed or to the web after formation, is obtained when the particulate is a solvent soluble particulate. Dissolving the soluble particulate in the solution would result in the incorporation of the material into the fiber without maintaining the particulate as a separate phase in the web. Adding the particulate to the web after formation preserves the solvent soluble material in its particulate form.

The web of the material can also have a gradient structure. In this disclosure, the term "gradient" indicates that some component (density, solidity, fiber size, etc.) of the web varies from one surface of the web to the opposite surface of the web. The gradient can be characterized by a variation in amount of active particulate, varying proportions of active and inert particulate, or other variation in particulate. The gradient can also be characterized in terms of a variation in the weight or the number of fibers. The gradient is formed by forming successively more or less fibers or more or less particulates within the web as the web is formed. Further, the concentration of spacer means or particulate can have a gradient aspect in which the size, weight or number of particulate materials per volume is substantially increased or reduced from one surface of the web to the other. The media of the invention can be used in the form of a single fine fiber web or a series of fine fiber webs in a filter structure.

The term "fine fiber" indicates a fiber having a fiber size or diameter of 0.001 to less than 5 microns or about 0.001 to less than 2 microns and, in some instances, 0.001 to 0.5 micron diameter. A variety of methods can be utilized for the manufacture of fine fiber. Chung et al., U.S. Pat. No. 6,743,273; Kahlbaugh et al., U.S. Pat. No. 5,423,892; McLead, U.S. Pat. No. 3,878,014; Barns, U.S. Pat. No. 4,650,506; Prentice, U.S. Pat. No. 3,676,242; Lohkamp et al., U.S. Pat. No. 3,841,953; and Butin et al., U.S. Pat. No. 3,849,241; all of which are incorporated by reference herein, disclose a variety of fine fiber technologies. The fine fiber of the invention is typically electrospun onto a substrate. The substrate can be a pervious or impervious material. In filtration applications non-woven filter media can be used as a substrate. In other applications the fiber can be spun onto an impervious layer and can be removed for down stream processing. In such an application, the fiber can be spun onto a metal drum or foil. The substrate can comprise an expanded PTFE layer or Teflon® layer. Such layers are useful in a variety of applications that can provide both filtration and activity from the active particulate.

For the purpose of this patent application, the term "adsorptive" indicates a particle that is active to adsorb and accumulate material from a fluid stream on the surface of a particle. The term "absorptive" indicates that the particle has the capacity to accumulate material from a fluid stream into the interior or void space or spaces within a particle. "Chemically reactive" indicates that the particulate has the capacity to react with and chemically change both the character of the particle and the chemical character of the material in the fluid stream. A "fluid stream", in this application, indicates either a gaseous or a liquid stream that can contain a particulate. The particulate can be either filtered from the fluid stream or the particulate can be adsorbed, absorbed or reacted with the particulate material of the invention. The term "active particulate", when used in this disclosure, refers to the absorptive, adsorptive or reactive particulate. The term "inert particulate" refers to a particulate that has no substantial absorptive, adsorptive or reactive capacity. Such particles can be used as a separation means or to occupy space.

For the purpose of this invention, the term "media" includes a structure comprising a web comprising a substantially continuous fine fiber mass and the separation or spacer materials of the invention dispersed in the fiber. In this disclosure the term "media" indicates the web of the invention, comprising the fine fiber and dispersed particulate in combination with a substrate of some active or inert type disclosed herein. The term "element" indicates the combination of the "media" of the invention with another component including cartridge components in the form of (e.g.) cylinder or flat panel structures. In this disclosure, the term "web" includes a substantially continuous or contiguous fine fiber phase with spacer particulate phase. A continuous web is necessary to impose a barrier to the passage of a particulate contaminant loading in a mobile phase. A single web, two webs or multiple webs can be combined to make up the filter media of the invention.

"Figure of Merit" can be thought of as a benefit to cost ratio, where efficiency is the benefit, and normalized pressure drop ($\Delta P$) is the cost ($\Delta P$/media velocity). The "cost" is normalized so that one can compare Figures of Merit from tests run at different velocities. Figure of Merit is simply an index to compare media. Larger Figure of Merit values are better than small. The formula for calculating Figure of Merit is:

$$\text{Figure of Merit} = -\text{Ln(penetration)}/(\Delta P/\text{media face velocity})$$

In the equation presented above, $\Delta P$ is the pressure drop across the media and the unit used in the equation is cm Hg; media face velocity has the unit of cm/sec; Ln(penetration) is the natural logarithm of penetration. And penetration is defined as:

Penetration=1−Efficiency

The standard units of measure which Figure of Merit is reported in are given below:

1/(cm Hg)/(cm/sec) or (cm/sec)/cm Hg

In many applications, especially those involving relatively high flow rates, an alternative type of filter media, sometimes generally referred to as "depth" media, is used. A typical depth media comprises a relatively thick tangle of fibrous material. Depth media is generally defined in terms of its porosity, density or percent solids content. For example, a 2-3% solidity media would be a depth media mat of fibers arranged such that approximately 2-3% of the overall volume comprises fibrous materials (solids), the remainder being air or gas space.

The fine fiber layers formed on the substrate in the filters of the invention should be substantially uniform in particulate distribution, filtering performance and fiber distribution. By substantial uniformity, we mean that the fiber has sufficient coverage of the substrate to have at least some measurable filtration efficiency throughout the covered substrate. The media of the invention can be used in laminates with multiple webs in a filter structure. The media of the invention includes at least one web of a fine fiber structure. The substrate upon which the fine fiber and active particulate can be formed can be either active or inactive substrate. Such substrates can have incorporated into the substrate layer active materials in the form of coatings, particulates, or fibers that can add adsorbent/absorbent or reactive properties to the overall structure. The overall thickness of the fiber web is about 1 to 100 times the fiber diameter or about 1 to 300 micron or about 5 to 200 microns. The web can comprise about 5 to 95 wt.-% fiber and about 95 to 5 wt.-% active particulate or about 30 to 75 wt.-% fiber and about 70 to 25 wt.-% active particulate occupies about 0.1 to 50 vol % of the layer or about 1 to 50 vol % or 2 to 50 vol % of the layer. The overall solidity (including the contribution of the active or inactive particulate) of the media is about 0.1 to about 50%, preferably about 1 to about 30%. The solidity of the web without including the contribution of the particulate in the structure is about 10 to about 80%. The filter media of the invention can attain a filtration efficiency of about 20 to about 99.9999% when measured according to ASTM-1215-89, with 0.78μ monodisperse polystyrene spherical particles, at 13.21 fpm (4 meters/min) as described herein. When used in HEPA type application, the filter performance is about 99.97% efficiency at 10.5 fpm and 0.3 micron NaCl or DOP particle size. Efficiency numbers in respect to this type of efficiency testing (0.3 micron DOP at 10.5 fpm test velocity), yield an efficiency in the range of 20 to 99.9999%

M The Figure of Merit can range from 10 to $10^5$. The filtration web of the invention typically exhibits a Frazier permeability test that would exhibit a permeability of at least about 1 meters-minutes$^{-1}$, preferably about 5 to about 50 meters-minutes$^{-1}$ When used as a inactive particulate or separation means, the particulate that characterizes the particulate phase of the web of the invention is a particulate that is either inert to the mobile phase and the entrained contaminant load or has some defined activity with respect to the mobile fluid or the load.

The particulate materials of the invention have dimensions capable of improving both the filtration properties of the media and the active reactive, absorbent or adsorbent character of the structures of the invention. The materials can be made of a variety of useful materials. The materials can either be substantially inert to the mobile phase and entrained particulate load passing through the web or the materials can interact with the fluid or particulate loading. In an "inert" mode, the spacer particulate simply alters the physical parameters of the fiber layer and the media including one or more fiber layers. When using a particulate that interacts with the fluid or the particulate loading, the particulate can, in addition to altering the physical properties of the media or layers, react with or absorb or adsorb a portion of either the mobile fluid or the particulate loading for the purpose of altering the material that passes through the web. The primary focus of the technology disclosed herein is to improve the physical structure and absorptive, reactive or adsorptive character of the media or layers and to improve filter performance. For that purpose, an active or an inert particle can be used. In certain applications, a substantially inert particle can be used in combination with a particulate that interacts with the mobile phase or particulate loading. In such applications, a combination of an inert particle and an interactive particle will be used. Such a combination of active particulate and inert particulate can provide both improved filter property and absorption, or adsorption properties.

The preferred fiber separation active, adsorptive or absorptive, means comprises a particulate. Such a particulate, used in the unique filter structures of the invention, occupies space within the filter layer or mat, reduces the effective density of the fiber, increases the tortuous pathways of the fluid through the filter and absorbs, adsorbs or reacts with the fluid or materials dissolved or dispersed in the fluid. Alternatively, the particulate can provide the mechanical space holding effect while additionally chemically reacting with the mobile fluid or adsorbing or absorbing gaseous, liquid or solid components in the mobile fluid. The active layer of the invention can comprise a nanofiber layer and dispersed within the nanofiber layer, the reactive, absorptive, or adsorptive particulate of the invention. The nanofiber layers of the invention typically range from about 0.5 to about 300 microns, 1 to about 250 microns or 2 to about 200 microns in thickness and contain within the layer about 0.1 to about 50 or 10 to about 50 vol % of the layer in the form of both inert (if any) and the active particulate of the invention. In this case, the active particulate of the invention can be combined with inert spacer particulate in some amount. The active particulate of the invention acting to absorb, adsorb or react with contaminants within the fluid flow while the inert particulate simply provides an excluded volume within the layer to reduce solidity, improve efficiency and other filtration properties.

The creation of low pressure drop active particulate, chemically reactive, absorptive, or adsorptive substrates for the removal of gas phase contaminants from airstreams is from flat sheet rolls of absorptive/adsorptive/reactive media that are layered or rolled together with a spacer media to form an adsorptive/reactive substrate with open channels and absorptive/adsorptive/reactive walls. Additionally, the spacer media can be made to be absorptive/adsorptive/reactive so as to contribute to the overall life/performance of the final chemical unit. The spacer media that creates the open channels can be created from a mesh, single lines of a polymer bead, glue dots, metal ribs, corrugated wire/polymer/paper mesh, corrugated metal/paper/polymer sheets, strips of polymer, strips of adhesive, strips of metal, strips of ceramic, strips of paper, or even from dimples placed in the media surface. These spacer media can be made absorptive/adsorptive/reactive by coating them or extruding/forming them with/from absorptive/adsorptive/reactive materials. The contaminated airflow is primarily directed along the channel created by the spacer media. This air comes into contact with the adsorptive/reactive media walls and/or spacer media and subsequently becomes adsorbed or reacted. The channel size and shape is controlled by the shape and size of the space media. Examples include squares, rectangles, triangles, and obscure shapes that may be created by a dotted pattern of polymer/adhesive. The chemistry of the walls and spacer media can be made specific to adsorb acidic, basic, and organic and water vapors, as well as several specific classes of compounds including reactive carbonyl compounds, including formaldehyde, acetaldehyde and acetone.

The reactive material can begin in many forms or functions. These forms include layers of reactive particles attached to a substrate. The reactive materials can be held together with adhesive or fibers to encapsulate, or simply hold, the particles and/or additional scrim materials are attached to hold the reactive material in place and minimize shedding of particles. The reactive material can also be sandwiched between layers of scrim. The scrim could help to produce the channels or space between the layers. This could be accomplished with a high loft scrim material that would give the proper spacing as well as ability to hold all the reactive particles in the media. The reactive or adsorptive particles can be held together or interspersed with fibers. The combination of particles and fibers (also nanofibers) results in a material that offers several advantages: increased diffusion; allowing for the use of smaller particles, thereby increasing the external surface area and hence the reaction rate; increased permeation into the reactive layer; the combination of particle and chemical filtration into a single layer; and the direct application of reactants to a filtration application without the need of a substrate or carrier (i.e. impregnated adsorbent).

Besides using particles that have been impregnated or coated with reactive species, it is obvious to anyone skilled in the art that these modifications can be performed after forming the fibrous web and structures. Imparting reactive activity to the particles and web after forming the fibrous web and structure can be accomplished using many different coating processes. For example, spray coating, dip coating, aerosol deposition, chemical vapor deposition, Kiss coating, and vacuum coating. A final step may involve a drying process that may, or may not, include thermal treatments, gas purging, or vacuum methods.

Specific Aspects:

A first aspect of the invention involves the use of a rolled substrate of an active particulate such as an activated carbon from KX Industries (trade name PLEXX) rolled with a nylon mesh to create a low pressure drop volatile organic chemical filter. Similar activated carbon substrates in flat sheets, or rolled good forms are available from other suppliers and can be applied in a similar manner. The material needs to be able to maintain the shape and flexibility to be able to form the various filter elements and minimize the shedding of particles. Another aspect of the invention involves the use of nanofibers and an active particulate such as an activated carbon powder co-dispersed into an air stream, or chamber, and deposited onto a substrate that can be any thin, flexible, porous substrate (e.g. a scrim, paper, mesh, etc.). The nanofibers entrap, or hold, the adsorptive particles in a thin layer and, as such, minimize the shedding of particles. This entire combination of substrate layer and nanofiber/adsorbent layer is then rolled with a spacer layer that provides non-restrictive channels for air flow or transport. The layer can comprise a mix of particulates that each react with a different chemical species. For example, activated carbon may also contain an impregnant that is specific for acidic, basic, or reactive organic contaminants. Examples include, citric acid for the removal of amines and ammonia, potassium hydroxide for the removal of sulfur dioxide and other acid gases, and 2,4-dinitrophenylhydrazine for the removal of carbonyl containing compounds. A third aspect of the invention is the use of nanofibers and citric acid powder, or granules, co-dispersed into an air stream, or chamber, and deposited onto a substrate that can be any thin, flexible, porous substrate (e.g. a scrim, paper, mesh, etc.).

Still another aspect of the invention involves the use of catalytic $TiO_2$ particles, fibers, or layers, in the element of the invention. Such catalytic layers, when irradiated with UV light, can cause a chemical reaction between the catalyst and materials entrapped in the mobile phase, and can remove the materials or change them from a noxious or harmful material into a benign material. Ambient light with some proportion of UV (less than 350 nm) and visible radiation (about 350 to 700 nm) can often be the source of sufficient radiation energy to obtain the catalytic effect for the $TiO_2$ in the element. If ambient conditions are insufficient for activity the element can be used with a separate UV source. Fluorescent UV sources are known and can be used either as a separate irradiating source, or can be incorporated into the element to provide substantial amount of UV radiation onto the $TiO_2$.

The nanofiber entraps, or holds the reactive particles in a thin layer, and as such, minimizes the shedding of particles. This entire combination of substrate layer and nanofiber/adsorbent layer is then rolled with a spacer layer that provides non-restrictive channels for air flow or transport. The fine fiber layer that contains the active particulate dispersed within the layer can be made from a variety of polymeric species. Since polymer species include a vast array of polymer materials. The polymer can be a single polymer species or blend of polymeric species or a polymer alloy of two or more polymer species. The fibers can be made using any known fine fiber manufacturing technique that involves combining polymers, if necessary with other polymers or additives, and then using a forming technique to shape the polymer into the fine fiber polymer desired. A 48%-52 wt % blend ratio between the polymer in example 1 and the polymer in example 2 respectively was used.

A further aspect of the invention is the use of nanofibers and ion-exchange resins, or granules co-dispersed into an air stream, or chamber, and deposited onto a substrate that can be any thin, flexible, porous substrate (e.g. a scrim, paper, mesh, etc.). The nanofibers entrap, or hold, the reactive particles in a thin layer and, as such, minimize the shedding of particles. This entire combination of substrate layer and nanofiber/adsorbent layer is then rolled with a spacer layer that provides non-restrictive channels for air flow or transport.

Polymer materials that can be used as the fiber polymer compositions of the invention include both addition polymer and condensation polymer materials such as polyolefin, polyacetal, polyamide, polyester, cellulose ether and ester, polyalkylene sulfide, polyarylene oxide, polysulfone, modified polysulfone polymers and mixtures thereof. Preferred materials that fall within these generic classes include polyethylene, polypropylene, poly(vinylchloride), polymethylmethacrylate (and other acrylic resins), polystyrene, and copolymers thereof (including ABA type block copolymers), poly(vinylidene fluoride), poly(vinylidene chloride), polyvinylalcohol in various degrees of hydrolysis (80% to 99.5%) in crosslinked and non-crosslinked forms. Preferred addition polymers tend to be glassy (a Tg greater than room temperature). This is the case for polyvinylchloride and polymethylmethacrylate, polystyrene polymer compositions or alloys or low in crystallinity for polyvinylidene fluoride and polyvinylalcohol materials. One class of polyamide condensation polymers are nylon materials. The term "nylon" is a generic name for all long chain synthetic polyamides. Typically, nylon nomenclature includes a series of numbers such as in nylon-6,6 which indicates that the starting materials are a $C_6$ diamine and a $C_6$ diacid (the first digit indicating a $C_6$ diamine and the second digit indicating a $C_6$ dicarboxylic acid compound). Nylon can be made by the polycondensation of ε-caprolactam in the presence of a small amount of water. This reaction forms a nylon-6 (made from a cyclic lactam—also known as ε-aminocaproic acid) that is a linear polyamide. Further, nylon copolymers are also contemplated. Copolymers can be made by combining various diamine compounds, various diacid compounds and various cyclic lactam structures in a reaction mixture and then forming the nylon with randomly positioned monomeric materials in a polyamide structure. For example, a nylon 6,6-6,10 material is a nylon manufactured from hexamethylene diamine and a $C_6$ and a $C_{10}$ blend of diacids. A nylon 6,6-6,6,10 is a nylon manufactured by copolymerization of ε-aminocaproic acid, hexamethylene diamine and a blend of a $C_6$ and a $C_{10}$ diacid material.

Block copolymers are also useful in the process of this invention. With such copolymers the choice of solvent swelling agent is important. The selected solvent is such that both blocks were soluble in the solvent. One example is a ABA (styrene-EP-styrene) or AB (styrene-EP) polymer in methylene chloride solvent. If one component is not soluble in the solvent, it will form a gel. Examples of such block copolymers are Kraton® type of styrene-b-butadiene and styrene-b-hydrogenated butadiene(ethylene propylene), Pebax® type of E-caprolactam-b-ethylene oxide, Sympatex® polyester-b-ethylene oxide and polyurethanes of ethylene oxide and isocyanates.

Addition polymers like polyvinylidene fluoride, syndiotactic polystyrene, copolymer of vinylidene fluoride and hexafluoropropylene, polyvinyl alcohol, polyvinyl acetate, amorphous addition polymers, such as poly(acrylonitrile) and its copolymers with acrylic acid and methacrylates, polystyrene, poly(vinyl chloride) and its various copolymers, poly (methyl methacrylate) and its various copolymers, can be solution spun with relative ease because they are soluble at low pressures and temperatures. However, highly crystalline polymer like polyethylene and polypropylene require high temperature, high pressure solvent if they are to be solution spun. Therefore, solution spinning of the polyethylene and polypropylene is very difficult. Electrostatic solution spinning is one method of making nanofibers and microfiber.

The polyurethane (PU) polyether used in this layer of invention can be an aliphatic or aromatic polyurethane depending on the isocyanate used and can be a polyether polyurethane or a polyester polyurethane. A polyether urethane having good physical properties can be prepared by melt polymerization of a hydroxyl-terminated polyether or polyester intermediate and a chain extender with an aliphatic or aromatic (MDI) diisocyanate. The hydroxyl-terminated polyether has alkylene oxide repeat units containing from 2 to 10 carbon atoms and has a weight average molecular weight of at least 1000. The chain extender is a substantially non-branched glycol having 2 to 20 carbon atoms. The amount of the chain extender is from 0.5 to less than 2 mole per mole of hydroxyl terminated polyether. It is preferred that the polyether polyurethane is thermoplastic and has a melting point of about 140° C. to 250° C. or greater (e.g., 150° C. to 250° C.) with 180° C. or greater being preferred.

In a first mode, the polyurethane polymer of the invention can be made simply by combining a di-, tri- or higher functionality aromatic or aliphatic isocyanate compound with a polyol compound that can comprise either a polyester polyol or a polyether polyol. The reaction between the active hydrogen atoms in the polyol with the isocyanate groups forms the addition polyurethane polymer material in a straight forward fashion. The OH:NCO ratio is typically about 1:1 leaving little or no unreacted isocyanate in the finished polymer. In any unreacted isocyanate compound, reactivity can be scavenged using isocyanate reactive compounds. In a second mode, the polyurethane polymer can be synthesized in a stepwise fashion from isocyanate terminated prepolymer materials. The polyurethane can be made from an isocyanate-terminated polyether or polyester. An isocyanate-capped polyol prepolymer can be chain-extended with an aromatic or aliphatic dihydroxy compound. The term "isocyanate-terminated polyether or polyurethane" refers generally to a prepolymer which comprises a polyol that has been reacted with a diisocyanate compound (i.e., a compound containing at least two isocyanate (—NCO) groups). In preferred form, the prepolymer has a functionality of 2.0 or greater, an average molecular weight of about 250 to 10,000 or 600-5000, and is prepared so as to contain substantially no unreacted monomeric isocyanate compound. The term "unreacted isocyanate compound" refers to free monomeric aliphatic or aromatic isocyanate-containing compound, i.e., diisocyanate compound which is employed as a starting material in connection with the preparation of the prepolymer and which remains unreacted in the prepolymer composition.

The term "polyol" as used herein, generally refers to a polymeric compound having more than one hydroxy (—OH) group, preferably an aliphatic polymeric (polyether or polyester) compound which is terminated at each end with a hydroxy group. The chain-lengthening agents are difunctional and/or trifunctional compounds having molecular weights of from 62 to 500 preferably aliphatic diols having from 2 to 14 carbon atoms, such as, for example, ethanediol, 1,6-hexanediol, diethylene glycol, dipropylene glycol and, especially, 1,4-butanediol. Also suitable, however, are diesters of terephthalic acid with glycols having from 2 to 4 carbon atoms, such as, for example, terephthalic acid bis-ethylene glycol or 1,4-butanediol, hydroxy alkylene ethers of hydroquinone, such as, for example, 1,4-di(B-hydroxyethyl)-hydroquinone, (cyclo)aliphatic diamines, such as, for example, isophorone-diamine, ethylenediamine, 1,2-, 1,3-propylene-diamine, N-methyl-1,3-propylene-diamine, N,N'-dimethyl-ethylene-diamine, and aromatic diamines, such as, for example, 2,4- and 2,6-toluoylene-diamine, 3,5-diethyl-2, 4- and/or -2,6-toluoylene-diamine, and primary ortho- di-, tri- and/or tetra-alkyl-substituted 4,4'-diaminodiphenyl-methanes. It is also possible to use mixtures of the above-mentioned chain-lengthening agents. Preferred polyols are polyesters, polyethers, polycarbonates or a mixture thereof. A wide variety of polyol compounds is available for use in the preparation of the prepolymer. In preferred embodiments, the polyol may comprise a polymeric diol including, for example, polyether diols and polyester diols and mixtures or copolymers thereof. Preferred polymeric diols are polyether diols, with polyalkylene ether diols being more preferred. Exemplary polyalkylene polyether diols include, for example, polyethylene ether glycol, polypropylene ether glycol, polytetramethylene ether glycol (PTMEG) and polyhexamethylene ether glycol and mixtures or copolymers thereof. Preferred among these polyalkylene ether diols is PTMEG. Preferred among the polyester diols are, for example, polybutylene adipate glycol and polyethylene adipate glycol and mixtures or copolymers thereof. Other polyether polyols may be prepared by reacting one or more alkylene oxides having from 2 to 4 carbon atoms in the alkylene radical with a starter molecule containing two active hydrogen atoms bonded therein. The following may be mentioned as examples of alkylene oxides: ethylene oxide, 1,2-propylene oxide, epichlorohydrin and 1,2- and 2,3-butylene oxide. Preference is given to the use of ethylene oxide, propylene oxide and mixtures of 1,2-propylene oxide and ethylene oxide. The alkylene oxides may be used individually, alternately in succession, or in the form of mixtures. Starter molecules include, for example: water, amino alcohols, such as N-alkyldiethanolamines, for example N-methyl-diethanolamine, and diols, such as ethylene glycol, 1,3-propylene glycol, 1,4-butanediol and 1,6-hexanediol. It is also possible to use mixtures of starter molecules. Suitable polyether polyols are also the hydroxyl-group-containing polymerization products of tetrahydrofuran. Suitable polyester polyols may be prepared, for example, from dicarboxylic acids having from 2 to 12 carbon atoms, preferably from 4 to 6 carbon atoms, and polyhydric alcohols. Suitable dicarboxylic acids include, for example: aliphatic dicarboxylic acids, such as succinic acid, glutaric acid, adipic acid, suberic acid, azelaic acid and sebacic acid, and aromatic dicarboxylic acids, such as phthalic acid, isophthalic acid and terephthalic acid. The dicarboxylic acids may be used individually or in the form of mixtures, for example in the form of a succinic, glutaric and adipic acid mixture. It may be advantageous for the preparation of the polyester polyols to use, instead of the dicarboxylic acids, the corresponding dicarboxylic acid derivatives, such as carboxylic acid diesters having from 1 to 4 carbon atoms in the alcohol radical, carboxylic acid anhydrides or carboxylic acid chlorides. Examples of polyhydric alcohols are glycols having from 2 to 10, preferably from 2 to 6, carbon atoms, such as ethylene glycol, diethylene glycol, 1,4-butanediol, 1,5-pentanediol, 1,6-hexanediol, 1,10-decanediol, 2,2-dimethyl-1,3-propanediol, 1,3-propanediol and dipropylene glycol. According to the desired properties, the polyhydric alcohols may be used alone or, optionally, in admixture with one another. Also suitable are esters of carbonic acid with the mentioned diols, especially those having from 4 to 6 carbon atoms, such as 1,4-butanediol and/or 1,6-hexanediol, condensation products of (omega-hydroxycarboxylic acids, for example (omega-hydroxycaproic acid, and preferably polymerization products of lactones, for example optionally substituted ε-caprolactones. These are preferably used as polyester polyols ethanediol polyadipate, 1,4-butanediol polyadipate, ethanediol-1,4-butanediol polyadipate, 1,6-hexanediol neopentyl glycol polyadipate, 1,6-hexanediol-1,4-butanediol polyadipate and polycaprolactones. The polyester polyols have molecular weights of from 600 to 5000.

The number of average molecular weight of the polyols from which the polymer or prepolymers may be derived may range from about 800 to about 3500 and all combinations and subcombinations of ranges therein. More preferably, the number of average molecular weights of the polyol may range from about 1500 to about 2500, with number average molecular weights of about 2000 being even more preferred.

The polyol in the prepolymers can be capped with an isocyanate compound or can be fully reacted to the thermoplastic polyurethane (TPU). A wide variety of diisocyanate compounds is available for use in the preparation of the prepolymers of the present invention. Generally speaking, the diisocyanate compound may be aromatic or aliphatic, with aromatic diisocyanate compounds being preferred. Included among the suitable organic diisocyanates are, for example, aliphatic, cycloaliphatic, araliphatic, heterocyclic and aromatic diisocyanates, as are described, for example, in Justus Liebigs Annalen der Chemie, 562, pages 75 to 136. Examples of suitable aromatic diisocyanate compounds include diphenylmethane diisocyanate, xylene diisocyanate, toluene diisocyanate, phenylene diisocyanate, and naphthalene diisocyanate and mixtures thereof. Examples of suitable aliphatic diisocyanate compounds include dicyclohexylmethane diisocyanate and hexamethylene diisocyanate and mixtures thereof. Preferred among the diisocyanate compounds is MDI due, at least in part, to its general commercial availability and high degree of safety, as well as its generally desirable reactivity with chain extenders (discussed more fully hereinafter). Other diisocyanate compounds, in addition to those exemplified above, would be readily apparent to one of ordinary skill in the art, once armed with the present disclosure. The following may be mentioned as specific examples: aliphatic diisocyanates, such as hexamethylene diisocyanate, cycloaliphatic diisocyanates, such as isophorone diisocyanate, 1,4-cyclohexane diisocyanate, 1-methyl-2,4- and -2,6-cyclohexane diisocyanate and the corresponding isomeric mixtures, 4,4'-, 2,4'- and 2,2'-dicyclohexylmethane diisocyanate and the corresponding isomeric mixtures, and, preferably, aromatic diisocyanates, such as 2,4-toluoylene diisocyanate, mixtures of 2,4- and 2,6-toluoylene diisocyanate, 4,4'-, 2,4'- and 2,2'-diphenylmethane diisocyanate, mixtures of 2,4'- and 4,4'-diphenylmethane diisocyanate, urethane-modified liquid 4,4'- and/or 2,4'-diphenylmethane diisocyanates, 4,4'-diisocyanatodiphenylethane-(1,2) and 1,5-naphthylene diisocyanate. Preference is given to the use of 1,6-hexamethylene diisocyanate, isophorone diisocyanate, dicyclohexylmethane diisocyanate, diphenylmethane diisocyanate isomeric mixtures having a 4,4'-diphenylmethane diisocyanate content of greater than 96 wt. %, and especially 4,4'-diphenylmethane diisocyanate and 1,5-naphthylene diisocyanate.

For the preparation of the TPUs, the chain-extension components are reacted, optionally in the presence of catalysts, auxiliary substances and/or additives, in such amounts that the equivalence ratio of NCO groups to the sum of all the NCO-reactive groups, especially of the OH groups of the low molecular weight diols/triols and polyols, is from 0.9:1.0 to 1.2:1.0, preferably from 0.95:1.0 to 1.10:1.0. Suitable catalysts, which in particular accelerate the reaction between the NCO groups of the diisocyanates and the hydroxyl groups of the diol components, are the conventional tertiary amines known in the prior art, such as, for example, triethylamine, dimethylcyclohexylamine, N-methylmorpholine, N,N'-dimethyl-piperazine, 2-(dimethylaminoethoxy)-ethanol, diazabicyclo-(2,2,2)-octane and the like, as well as, especially, organometallic compounds such as titanic acid esters, iron compounds, tin compounds, for example tin diacetate, tin dioctate, tin dilaurate or the tindialkyl salts of aliphatic carboxylic acids, such as dibutyltin diacetate, dibutyltin dilaurate or the like. The catalysts are usually used in amounts of from 0.0005 to 0.1 part per 100 parts of polyhydroxy compound. In addition to catalysts, auxiliary substances and/or additives may also be incorporated into the chain-extension components. Examples which may be mentioned are lubricants, antiblocking agents, inhibitors, stabilizers against hydrolysis, light, heat and discoloration, flameproofing agents, colorings, pigments, inorganic and/or organic fillers and reinforcing agents. Reinforcing agents are especially fibrous reinforcing materials such as, for example, inorganic fibers, which are prepared according to the prior art and may also be provided with a size.

Further additional components that may be incorporated into the PU are thermoplastics, for example polycarbonates and acrylonitrile-butadiene-styrene terpolymers, especially ABS. Other elastomers, such as, for example, rubber, ethylene-vinyl acetate polymers, styrene-butadiene copolymers and other PUs, may likewise be used. Also suitable for incorporation are commercially available plasticisers such as, for example, phosphates, phthalates, adipates, sebacates. The PUs according to the invention are produced continuously. Either the known band process or the extruder process may be used. The components may be metered simultaneously, i.e. one shot, or in succession, i.e. by a prepolymer process. In that case, the prepolymer may be introduced either batchwise or continuously in the first part of the extruder, or it may be prepared in a separate prepolymer apparatus arranged upstream. The extruder process is preferably used, optionally in conjunction with a prepolymer reactor.

Fiber can be made by conventional methods and can be made by melt spinning the polyurethane PU or a mixed polyether urethane and the additive. Melt spinning is a well known process in which a polymer is melted by extrusion, passed through a spinning nozzle into air, solidified by cooling, and collected by winding the fibers on a collection device. Typically the fibers are melt-spun at a polymer temperature of about 150° C. to about 300° C.

Polymeric materials have been fabricated in non-woven and woven fabrics, fibers and microfibers. The polymeric material provides the physical properties required for product stability. These materials should not change significantly in dimension, suffer reduced molecular weight, become less flexible or subject to stress cracking, or physically deteriorate in the presence of sunlight, humidity, high temperatures or other negative environmental effects. The invention relates to an improved polymeric material that can maintain physical properties in the face of incident electromagnetic radiation such as environmental light, heat, humidity and other physical challenges.

We have also found a substantial advantage to forming polymeric compositions comprising two or more polymeric materials in polymer admixture, alloy format, or in a crosslinked chemically bonded structure. We believe such polymer compositions improve physical properties by changing polymer attributes such as improving polymer chain flexibility or chain mobility, increasing overall molecular weight and providing reinforcement through the formation of networks of polymeric materials.

In one embodiment of this concept, two related or unrelated polymer materials can be blended for beneficial properties. For example, a high molecular weight polyvinylchloride can be blended with a low molecular weight polyvinylchloride. Similarly, a high molecular weight nylon material can be blended with a low molecular weight nylon material. Further, differing species of a general polymeric genus can be blended. For example, a high molecular weight styrene material can be blended with a low molecular weight, high impact polystyrene. A nylon-6 material can be blended with a nylon copolymer such as a nylon-6,6-6,6,10 copolymer. Further, a polyvinylalcohol having a low degree of hydrolysis such as an 80-87% hydrolyzed polyvinylalcohol can be blended with a fully or superhydrolyzed polyvinylalcohol having a degree of hydrolysis between 98 and 99.9% and higher. All of these materials in admixture can be crosslinked using appropriate crosslinking mechanisms. Nylons can be crosslinked using crosslinking agents that are reactive with the nitrogen atom in the amide linkage. Polyvinylalcohol materials can be crosslinked using hydroxyl reactive materials such as monoaldehydes, such as formaldehyde, ureas, melamine-formaldehyde resin and its analogues, boric acids and other inorganic compounds. dialdehydes, diacids, urethanes, epoxies and other known crosslinking agents. Crosslinking technology is a well known and understood phenomenon in which a crosslinking reagent reacts and forms covalent bonds between polymer chains to substantially improve molecular weight, chemical resistance, overall strength and resistance to mechanical degradation.

We have found that additive materials can significantly improve the properties of the polymer materials in the form of a fine fiber. The resistance to the effects of heat, humidity, impact, mechanical stress and other negative environmental effect can be substantially improved by the presence of additive materials. We have found that while processing the microfiber materials of the invention, the additive materials can improve the oleophobic character, the hydrophobic character, and can appear to aid in improving the chemical stability of the materials. We believe that the fine fibers of the invention in the form of a microfiber are improved by the presence of these oleophobic and hydrophobic additives as these additives form a protective layer coating, ablative surface or penetrate the surface to some depth to improve the nature of the polymeric material. We believe the important characteristics of these materials are the presence of a strongly hydrophobic group that can preferably also have oleophobic character. Strongly hydrophobic groups include fluorocarbon groups, hydrophobic hydrocarbon surfactants or blocks and substantially hydrocarbon oligomeric compositions. These materials are manufactured in compositions that have a portion of the molecule that tends to be compatible with the polymer material affording typically a physical bond or association with the polymer while the strongly hydrophobic or oleophobic group, as a result of the association of the additive with the polymer, forms a protective surface layer that resides on the surface or becomes alloyed with or mixed with the polymer surface layers. For 0.2-micron fiber with 10% additive level, the surface thickness is calculated to be around 50 Å, if the additive has migrated toward the surface. Migration is believed to occur due to the incompatible nature of the oleophobic or hydrophobic groups in the bulk material. A 50 Å thickness appears to be reasonable thickness for protective coating. For 0.05-micron diameter fiber, 50 Å thickness corresponds to 20% mass. For 2 microns thickness fiber, 50 Å thickness corresponds to 2% mass. Preferably the additive materials are used at an amount of about 2 to 25 wt. %. Oligomeric additives that can be used in combination with the polymer materials of the invention include oligomers having a molecular weight of about 500 to about 5000, preferably about 500 to about 3000 including fluoro-chemicals, nonionic surfactants and low molecular weight resins or oligomers. Examples of useful phenolic additive materials include Enzo-BPA, Enzo-BPA/phenol, Enzo-TBP, Enzo-COP and other related phenolics were obtained from Enzymol International Inc., Columbus, Ohio.

An extremely wide variety of fibrous filter media exist for different applications. The durable nanofibers and microfibers described in this invention can be added to any of the media. The fibers described in this invention can also be used to substitute for fiber components of these existing media giving the significant advantage of improved performance (improved efficiency and/or reduced pressure drop) due to their small diameter, while exhibiting greater durability.

Polymer nanofibers and microfibers are known; however, their use has been very limited due to their fragility to mechanical stresses, and their susceptibility to chemical degradation due to their very high surface area to volume ratio. The fibers described in this invention address these limitations and will therefore be usable in a very wide variety of filtration, textile, membrane, and other diverse applications.

A media construction according to the present invention includes a first layer of permeable coarse fibrous media or substrate having a first surface. A first layer of fine fiber media is secured to the first surface of the first layer of permeable coarse fibrous media. Preferably the first layer of permeable coarse fibrous material comprises fibers having an average diameter of at least 10 microns, typically and preferably about 12 (or 14) to 30 microns. Also preferably the first layer of permeable coarse fibrous material comprises a media having a basis weight of no greater than about 200 grams/meter$^2$, preferably about 0.50 to 150 g/m$^2$, and most preferably at least 8 g/m$^2$. Preferably the first layer of permeable coarse fibrous media is at least 0.0005 inch (12 microns) thick, and typically and preferably is about 0.001 to 0.030 inch (25-800 microns) thick. The element of the invention, including the fine fiber and dispersed particulate layer can be combined with a variety of other layers as discussed elsewhere in the specification. The layers can be made as a flat or coplanar sheet version of the layers of the invention or can be pleated, corrugated or formed into virtually any other cross-sectional shape needed to form the low pressure drop flow through element of the invention. The substrate can comprise an expanded poly PTFE layer or Teflon layer. The substrate can also be substantially free of a Teflon, an expanded poly PTFE layer, or stretched PTFE fiber or layer. Such layers are useful in a variety of in use applications that can provide both filtration and activity from the active particulate. Such layers can also aid in confining the particulate into the element.

In preferred arrangements, the first layer of permeable coarse fibrous material comprises a material which, if evaluated separately from a remainder of the construction by the Frazier permeability test, would exhibit a permeability of at least 1 meter(s)/min, and typically and preferably about 2-900 meters/min. Herein when reference is made to efficiency, unless otherwise specified, reference is made to efficiency when measured according to ASTM-1215-89, with 0.78μ monodisperse polystyrene spherical particles, at 20 fpm (6.1 meters/min) as described herein.

Preferably the layer of fine fiber material secured to the first surface of the layer of permeable coarse fibrous media is a layer of nano- and microfiber media wherein the fibers have average fiber diameters of no greater than about 2 microns, generally and preferably no greater than about 1 micron, and typically and preferably have fiber diameters smaller than 0.5 micron and within the range of about 0.05 to 0.5 micron. Also, preferably the first layer of fine fiber material secured to the first surface of the first layer of permeable coarse fibrous material has an overall thickness that is no greater than about 30 microns, more preferably no more than 20 microns, most preferably no greater than about 10 microns, and typically and preferably that is within a thickness of about 1-8 times (and more preferably no more than 5 times) the fine fiber average diameter of the layer.

The electrostatic spinning process can form the microfiber or nanofiber of the unit. A suitable apparatus for forming the fiber is illustrated in Barris U.S. Pat. No. 4,650,506. This apparatus includes a reservoir in which the fine fiber forming polymer solution is contained, a pump and a rotary type emitting device or emitter to which the polymeric solution is pumped. The emitter generally consists of a rotating union, a rotating portion including a plurality of offset holes and a shaft connecting the forward facing portion and the rotating union. The rotating union provides for introduction of the polymer solution to the forward facing portion through the hollow shaft. Alternatively, the rotating portion can be immersed into a reservoir of polymer fed by reservoir and pump. The rotating portion then obtains polymer solution from the reservoir and as it rotates in the electrostatic field, the electrostatic field aligned toward the collecting media accelerates a droplet of the solution as discussed below.

Facing the emitter, but spaced apart therefrom, is a substantially planar grid 60 upon which the collecting media (i.e. substrate or combined substrate is positioned. Air can be drawn through the grid. The collecting media is passed around rollers which are positioned adjacent opposite ends of grid. A high voltage electrostatic potential is maintained between emitter and grid by means of a suitable electrostatic voltage source and connections and which connect respectively to the grid and emitter.

In use, the polymer solution is pumped to the rotating union or reservoir from reservoir. The forward facing portion rotates while liquid exits from holes, or is picked up from a reservoir, and moves from the outer edge of the emitter toward collecting media positioned on the grid. Specifically, the electrostatic potential between grid and the emitter imparts a charge to the material that cause liquid to be emitted there from as thin fibers which are drawn toward grid where they arrive and are collected on substrate or an efficiency layer. In the case of the polymer in solution, solvent is evaporated from the fibers during their flight to the grid; therefore, the fibers arrive at the substrate or efficiency layer without substantial solvent. The fine fibers bond to the substrate fibers first encountered at the grid. Electrostatic field strength is selected to ensure that as the polymer material it is accelerated from the emitter to the collecting media, the acceleration is sufficient to render the material into a very thin microfiber or nanofiber structure. Increasing or slowing the advance rate of the collecting media can deposit more or less emitted fibers on the forming media, thereby allowing control of the thickness of each layer deposited thereon. The rotating portion can have a variety of beneficial positions. The rotating portion can be placed in a plane of rotation such that the plane is perpendicular to the surface of the collecting media or positioned at any arbitrary angle. The rotating media can be positioned parallel to or slightly offset from parallel orientation.

A sheet-like substrate is unwound at a station. The sheet-like substrate is then directed to a splicing station wherein multiple lengths of the substrate can be spliced for continuous operation. The continuous length of sheet-like substrate is directed to a fine fiber technology station comprising the spinning technology discussed above, wherein a spinning device forms the fine fiber and lays the fine fiber in a filtering layer on the sheet-like substrate. After the fine fiber layer is formed on the sheet-like substrate in the formation zone, the fine fiber layer and substrate are directed to a heat treatment station for appropriate processing. The sheet-like substrate and fine fiber layer is then tested in an efficiency monitor and nipped if necessary at a nip station. The sheet-like substrate and fiber layer is then steered to the appropriate winding station to be wound onto the appropriate spindle for further processing.

The element of the invention when used in a filtration mode should have a minimal pressure drop for acceptable function as a filter and to obtain the activity of the active particle(s). Such pressure drop information is known for the types of filtration devices of the invention. Such pressure drop parameters define the useful life of the filtration element of the invention. The element of the invention, when used in a flow through mode with no intervening filter layer, should provide little or no resistance to the flow of the mobile fluid through the element (e.g.; less 0.1 inches or less than 1-5 inches of water). Flow should not be constrained but the residence time, however, of the fluid within the element must be sufficient to obtain sufficient contact and absorbance/absorbance/reaction needed in the element to obtain the desired activity form the active particulate within the element. A useful residence time, depending on active particulate can be from about 0.01 to as long as it is necessary to obtain some removal of entrained materials. The residence time can be 0.02 second to as much as 5 minutes and typically ranges from about 0.01 to 60 seconds 0.01 to 1 second or as little as 0.02 to 0.5 second. The lifetime of such a unit is defined by the load of active particulate and the residual amount of activity in the unit. Some small amount of pressure drop can be designed into the element to slow the flow and extend residence time without substantially impeding flow.

The media, web, layers or elements of the invention can be regenerated. In the case of a reactive particulate in the invention, the particulate can be regenerated by chemically treating the particulate. In the case of absorptive or adsorptive particulate, the particulate can be generated by heating the element to a temperature sufficient to drive the absorbed or adsorbed material from the particulate surface or internal structure. The element can also be evacuated such that the effects of reduced pressure can remove the volatile material from the surface of the adsorptive particle or from the interior of the absorptive particle.

The reactive species can be regenerated by first removing any reaction byproducts from the reaction from the active species with the entering material in the fluid phase. In one such reaction, byproducts are removed, the particulate remaining within the element enhanced by passing a solution or suspension of the active material through the element, causing the interior structure including the fine fiber layer to accumulate additional amounts of reactive material.

EXEMPLARY SECTION

Example 1

A thermoplastic aliphatic polyurethane compound manufactured by Noveon®, TECOPHILIC SP-80A-150 TPU was used. The polymer is a polyether polyurethane made by reacting dicyclohexylmethane 4,4'-diisocyanate with a polyol.

Polymer Example 2

A copolymer of nylon 6,6,6-6,10 nylon copolymer resin (SVP-651) was analyzed for molecular weight by the end group titration. (J. E. Walz and G. B. Taylor, determination of the molecular weight of nylon, Anal. Chem. Vol. 19, Number 7, pp 448-450 (1947). The number of average molecular weight was between 21,500 and 24,800. The composition was estimated by the phase diagram of melt temperature of three component nylon, nylon 6 about 45%, nylon 66 about 20% and nylon 610 about 25%. (Page 286, Nylon Plastics Handbook, Melvin Kohan ed. Hanser Publisher, New York (1995)). Reported physical properties of SVP 651 resin are:

| Property | ASTM Method | Units | Typical Value |
| --- | --- | --- | --- |
| Specific Gravity | D-792 | — | 1.08 |
| Water Absorption (24 hr immersion) | D-570 | % | 2.5 |
| Hardness | D-240 | Shore D | 65 |
| Melting Point | DSC | ° C. (° F.) | 154 (309) |
| Tensile Strength @ Yield | D-638 | MPa (kpsi) | 50 (7.3) |
| Elongation at Break | D-638 | % | 350 |
| Flexural Modulus | D-790 | MPa (kpsi) | 180 (26) |
| Volume Resistivity | D-257 | ohm-cm | $10^{12}$ |

Polymer Example 3

Copolyamide (nylon 6,6-6,6,10) described earlier in Polymer Example 2 was mixed with phenolic resin, identified as Georgia Pacific 5137.

Nylon:Phenolic Resin Ratio and its Melt Temperature of Blends are Shown Here:

| Composition | Melting Temperature (F.°) |
| --- | --- |
| Polyamide:Phenolic = 100:0 | 150 |
| Polyamide:Phenolic = 80:20 | 110 |
| Polyamide:Phenolic = 65:35 | 94 |
| Polyamide:Phenolic = 50:50 | 65 |

Figure 1B:
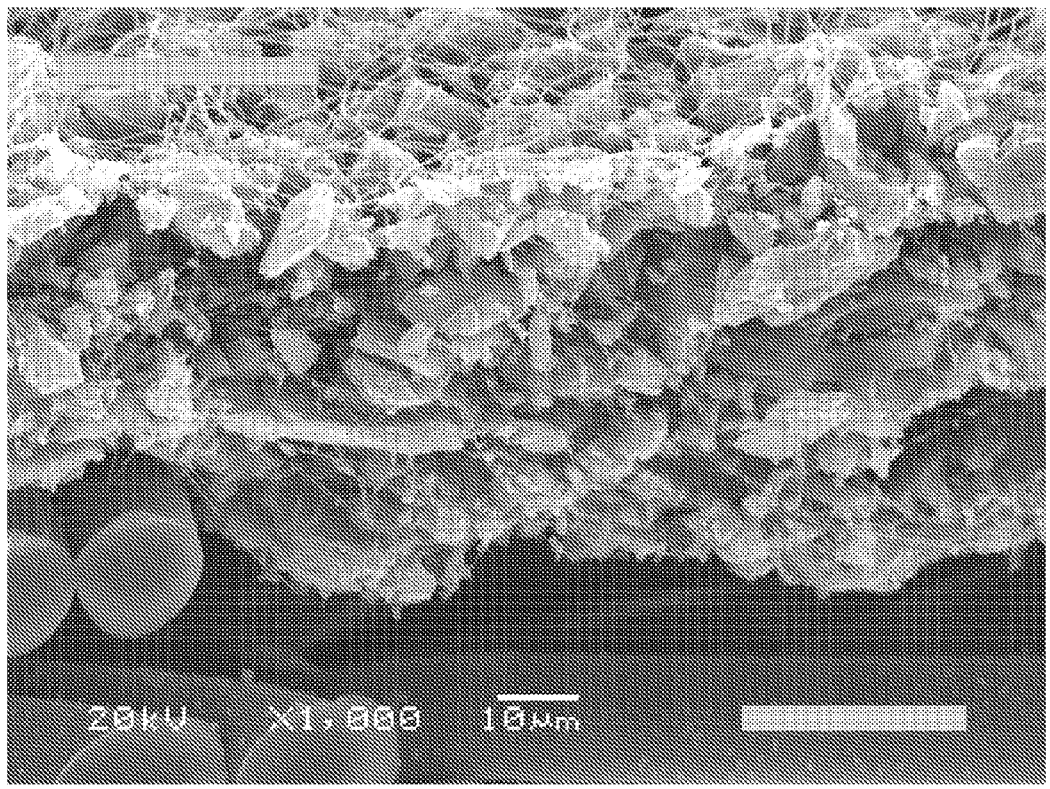
Figure 2:
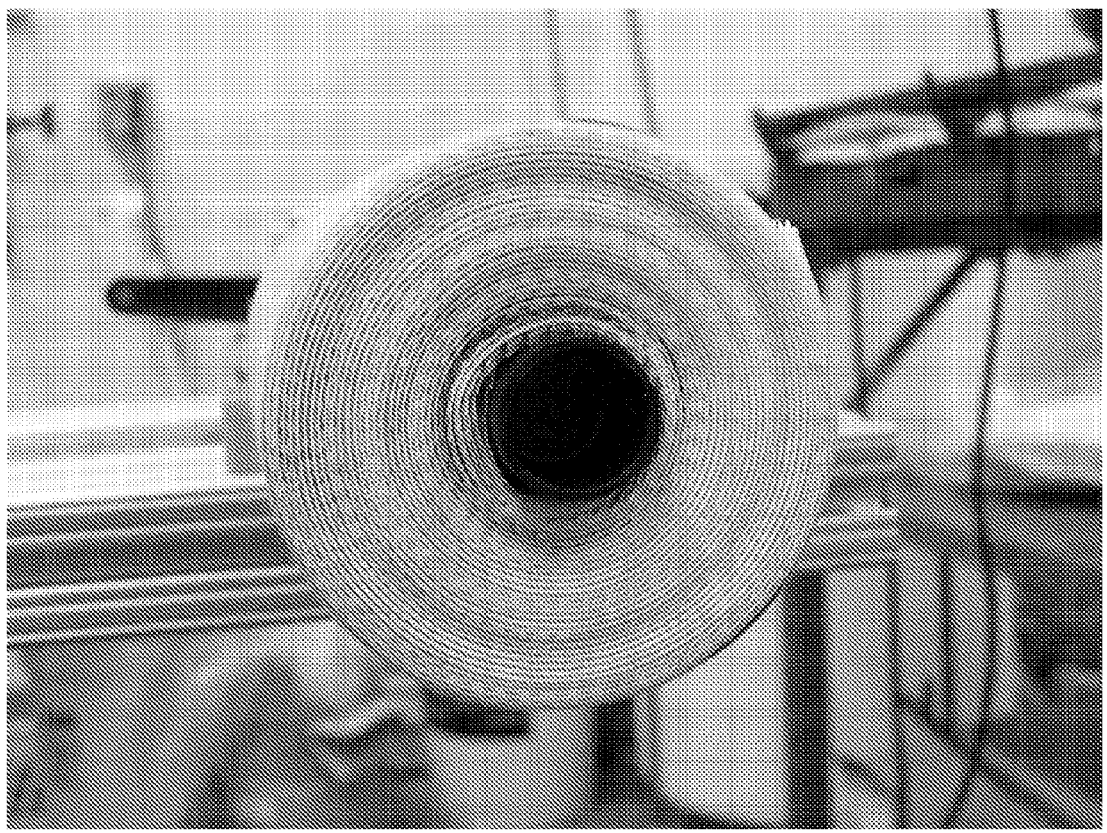
FIG. 2 is an end view of a spiral wound media that has a chemical filtration media wound with a plastic mesh screen for spacing the layers. Such a structure is a flow by structure having little or no filtration properties but having substantial reactive adsorptive or reactive capacity.

The elasticity benefit of this new fiber chemistry comes from the blend of a polymer with a polyurethane. The polyurethane used in this invention is polymer Ex. 1 obtained from Noveon, Inc. and is identified as TECOPHILIC SP-80A-150 Thermoplastic Polyurethane. This is an alcohol-soluble polymer and was dissolved in ethyl alcohol at 60° C. by rigorously stirring for 4 hours. After the end of 4 hours, the solution was cooled down to room temperature, typically overnight. The solids content of the polymer solution was around 13% wt, although it is reasonable to suggest that different polymer solids content can be used as well. Upon cooling down to room temperature, the viscosity was measured at 25° C. and was found to be around 340 cP. This solution was electrospun under varying conditions successfully. FIGS. 1A and 1B show a series of Scanning Electron Microscope (SEM) images showing the as-spun fibers along with some functional particles (SEM image).

In the field of chemical filtration, the particles displayed in the SEM image 1 (FIG. 1) provided above, are activated carbon particles intended for removal of certain chemicals in the gas phase. The adsorption capacity of these particles has a strong relationship with their post-process conditions. In electrospinning, the solvent vapor coming off from the electrospun fibers as they form and dry can be readily adsorbed by the carbon particles hence limiting their overall capacity. In order to "flush" the solvent molecules from the activated carbon particles, it is therefore necessary to heat the structure at a temperature beyond the boiling point of solvent, in this case 78-79° C., for an extended duration of time, to get any residual solvent off from the carbon particles. Consequently, these fibers should withstand these extreme temperatures during the post-treatment process in this example presented above.

To improve the temperature resistance of these fibers and at the same time to benefit from their high elasticity and tackiness (desired for attachment of active and/or non-active particles etc.), we have blended the polyurethane based polymer solution with a polymer solution polymer example 2 that is a polyamide-based solution Ultimately, we have used the 48/52% wt blend ratio between polymer example 1 and polymer example 2, respectively; the resulting solution had a viscosity of about 210 cP. The mixing was carried out at room temperature by simply stirring the blend vigorously for several minutes. Electrospinning of the blend was carried out using typically process. The as-spun fibers were then subjected to heating; in this case heating was carried out at 110° C. for 2 minutes.

The fibers electrospun from this polymer solution blend polymer example 1 and polymer example 2 have excellent temperature stability and good elasticity and tackiness, which are not possible to find all-in-one in any component of the solution, polymer example 1 and polymer example 2. The fibers have an average diameter about two to three times that of the average fiber diameter of polymer example 2 fibers (polymer example 2 average fiber diameter is in the range of 0.25 microns).

While this polyurethane has excellent elasticity, it is rather preferred to have temperature resistance as well. This is particularly important if there are subsequent downstream processes that require high temperature processing.

The polymer solution was as follows: the polymer had a melt flow index of 18.1 g/10 min measured at 180° C. The solution viscosity was measured as 210 cP at 25° C. using a viscometer.

Reemay 2011 polyester substrate was used to deposit the nanofiber/activated carbon particle composite. The substrate is very open, substrate fibers are laid down flat with no protrusion of fibers from the web and has a very low basis weight, 25 g/m$^2$. There can be a wide selection of different substrate materials suitable for the production of this nanofiber/activated carbon composite.

Activate carbon particles were dispersed to the nanofiber matrix using a deflocculator system, where the particles were fed to the deflocculator using a dry particle feeder (screw feeder) with electronic controls over the particle output rate.

Figure 4A:
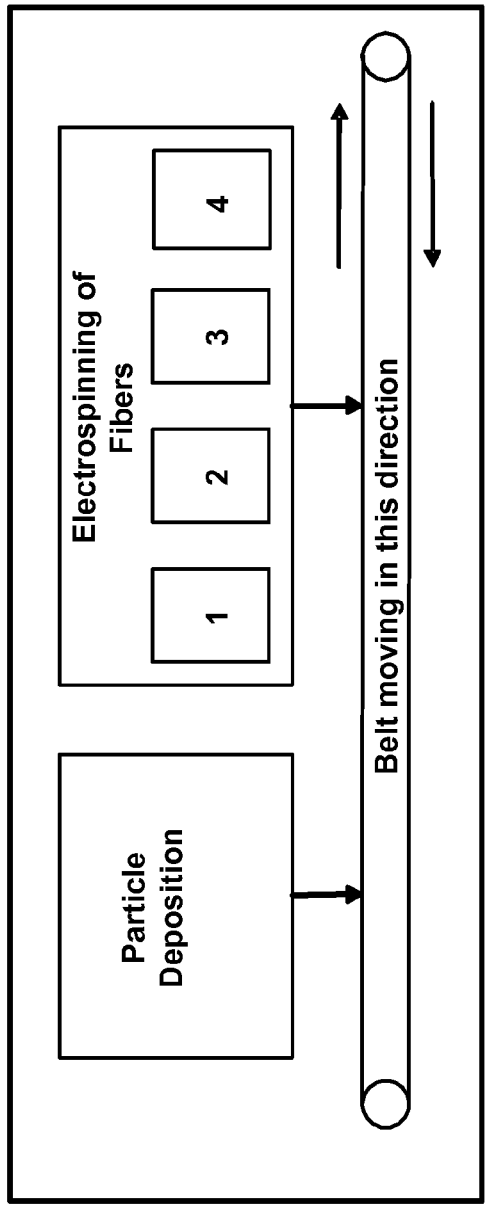
FIGS. 4A and B are graphical representation apparatus that can be used to form the fine fiber layers of the invention by combining particle deposition with electrospinning of the fine fiber from polymer solution.
Figure 4B:
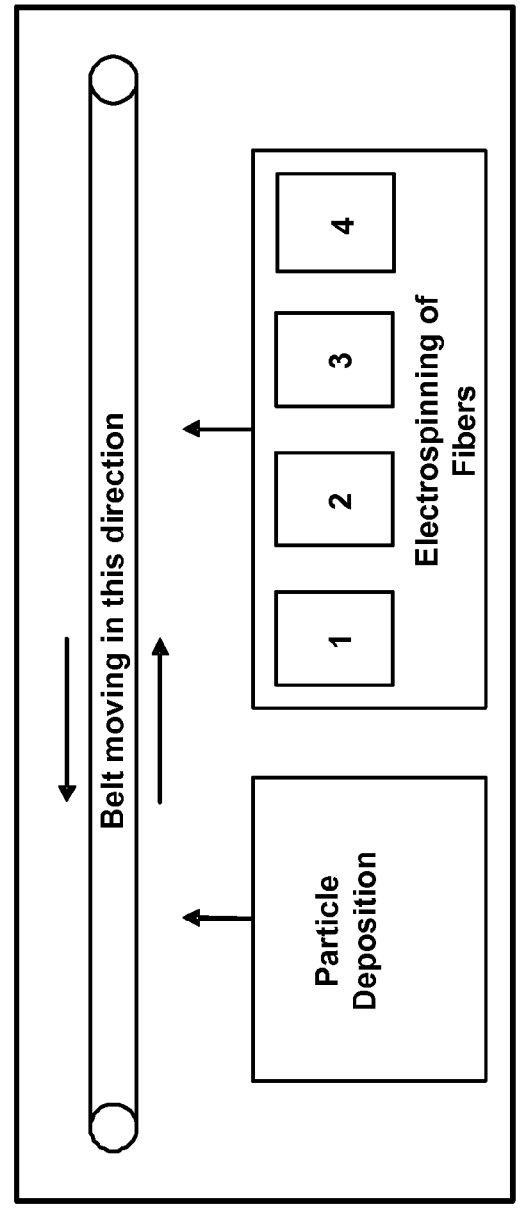

The substrate was mounted on a continuous belt (FIGS. 4a and 4b) and as such the composite was generated using a pilot machine with limited fiber spinning capability.

The following table summarizes the run cycle:

| Example | 0 sec | Start of the electrospinning of the polymer solution |
|---------|-------|------------------------------------------------------|
|         | 20 sec | Start of the particle deposition |
|         | 1260 sec | Amount of particle discharged is 60 g/Particle deposition stopped |
|         | 1290 sec | Only electrospinning of fibers from 1260 to 1290 sec/Electrospinning stopped |

Description of the Run Cycle Used for Generating the Nanofiber/Activated Carbon Particle Composite.

Quantification of the accurate amount of carbon inside the composite was carried out. To do that, the same polymer solution was electrospun for the same duration of time (1290 sec) onto the same Reemay 2011 substrate at the same processing parameters. Later, by cutting the same sample sizes (4 inch diameter), both samples (one with particles and the other one without) were weighed, and the difference between the two weighing provided us the activated carbon loading in the given surface area of the sample (1 m$^2$), we have calculated that the amount of activated carbon inside the composite was 56.04 g/m$^2$. In other words, out of 60 g of particle discharged from the feeder, 56 g was able to make it to the composite, whereas 4 g was lost in various ways including deposition to the inner surface of the nozzle that was used to deflect the particle trajectory.

Overall, the nanofiber/activated carbon particle composite was composed of 91.4 wt % of carbon particles and 8.6 wt % of polymeric nanofibers.

By applying the particles in this dry method, we have utilized a large portion of particles inside the composite, and furthermore the dry method of application allowed us to not block the particle surface area to the extent that it would effect the diffusion of the challenge gas into them.

There are two distinct mechanisms of capture of activated carbon particles in the nanofiber matrix:

Mechanical entanglement of the particles inside the nanofiber matrix that inhibit the particles from moving freely inside the composite. The result is a nanofiber network that acts much like a spider web, capturing and holding the particles on itself. As more layers are deposited, the network turns into a nanofibrous matrix of nanofiber and particles.

Adhesion between the particles and nanofibers as a direct result of solution spinning of the nanofibers. Because nanofibers were created from a polymer solution using electrospinning process, as the nanofibers land on the target, they may retain a very small amount of the solvent in their structure and hence they have the ability to fuse onto the activated carbon particles. Because the fibers have very small fiber diameter, and there are only a handful of nanofibers in contact with the particle, the available surface area of the activated carbon for chemical adsorption is dramatically high, enough to affect the performance of the media in a positive way.

The heat treatment at 230° F. for 5 minutes is carried out because during electrospinning of almost any polymer solution there could be a very small amount of residual solvent remaining in the nanofiber structure. In an attempt to eliminate any residual solvent, which could affect the adsorptive capacity of the activated carbon particles, we heated the composite beyond the boiling point of the solvent used to prepare the polymer solution. In this case, the boiling point of the solvent was around 176° F. at 760 mmHg. And thus heating at 230° F. for 5 minutes ensured the complete removal of any residual solvent from the nanofibers and/or the activated carbon particles.

Below is a table that outlines the results of the particulate efficiency testing conducted using TSI 3160 fractional efficiency test bench with dioctyl-phthalate particles in the 0.02-0.4 micron diameter range, at 10.5 ft/min face velocity. Efficiency, penetration and resistance are the outputs of the testing. This sample was tested after heating it at 230° F. for 5 minutes in a lab oven.

| Particle Size D (microns) | Eff. (%) | Pen. (%) | Res. (mm-$H_2O$) | FOM |
|---|---|---|---|---|
| 0.02 | 99.81 | 0.19 | 13.98 | 326 |
| 0.03 | 99.61 | 0.39 | 13.96 | 289 |
| 0.04 | 99.30 | 0.70 | 13.97 | 258 |
| 0.05 | 98.06 | 1.94 | 13.98 | 205 |
| 0.06 | 97.53 | 2.47 | 13.98 | 192 |
| 0.07 | 97.00 | 3.00 | 13.98 | 182 |
| 0.08 | 96.47 | 3.53 | 13.97 | 174 |
| 0.09 | 96.04 | 3.96 | 13.99 | 168 |
| 0.10 | 95.50 | 4.50 | 13.97 | 161 |
| 0.20 | 95.29 | 4.71 | 13.98 | 159 |
| 0.30 | 97.06 | 2.94 | 13.99 | 183 |
| 0.40 | 98.37 | 1.63 | 13.98 | 214 |

| | | |
|---|---|---|
| Carbon loading | g/$m^2$ | 56.04 |
| Carbon concentration | % | 91.40 |
| Total fiber and carbon composite | g/$m^2$ | 61.31 |

FOM (Figure of Merit) is calculated using these outputs and the face velocity of the test by the following formula:

Figure of Merit=−Ln(penetration)/(delta$P$/media face velocity)

The standard unit of measure of FOM is 1/(cm Hg)/(cm/sec) or (cm/sec)/cm Hg The higher the FOM, the better the quality of the media is; in other words, higher FOM means either higher efficiency for the same pressure drop, or lower pressure drop for the same efficiency.

From the table presented above, one can see that the particulate efficiency of this sample is in the high 90% range. It is very straightforward to generate composites with even higher particulate efficiency by several means:

Increasing the thickness of the overall composite

Keeping the thickness of the overall composite the same, however, adding high efficiency layer made of very fine (around 0.25 micron) nanofibers coated on the bottom and top of the nanofiber/activated carbon particle composite The second method is preferable, simply because it would allow keeping the chemi-adsorptive properties of the composite the same, while the particulate efficiency can be adjusted independently.

The application of this invention is to purify fluid streams, including liquid streams and gaseous streams. The filter element of the invention is placed in a location or environment suitable for a particular application, such that a contaminate-laded fluid stream can pass through or pass by the element, and contaminates can be removed. Fluid streams for the application include liquid or gaseous streams that can contain contaminates such as dust particulate, water, solvent residue, oil residue, mixed aqueous oil residue, harmful gases. Mobile liquid streams include fuels, oils, solvent streams, etc. The streams are contacted with the flow-through or flow-by structures of the invention to remove liquid or particulate contaminants, color forming species, and soluble impurities. The contaminates to be removed by application of the invention also include biological products such as, for example, prions, viruses, bacteria, spores, nucleic acids, other potentially harmful biological products or hazardous materials.

In aspects. the invention can be used to purify fluid streams, with some further addition of liquid filtration including fuel and lubes, water filtration air streams in any application that requires airborne acidic, basic and volatile organic gaseous filtration at relatively low gas concentrations (<100 ppm). The application environments may consist of either a stagnant or flowing gas stream that is either dry or contains significant amounts of water. One of the primary applications for this invention is to have a light weight, low pressure drop adsorbent media for semiconductor applications that require purified air to be provided to a process, tool, test, or enclosure. This may include other applications that require purified air, nitrogen, or other process gas stream. The adsorbent media is capable of removing gaseous contamination within clean rooms, semiconductor industry or sub-fabrication system, process tools, and enclosures through single pass, recirculation, or static filtration. Additionally, the media can purify air that is taken from one location to another. Such air transfer can be from a sub-fabrication to the main fabrication, or from the external atmosphere to an emission test system.

In one aspect, the filter element of the invention can be placed in a vent for an enclosure, such that the interior of the enclosure is maintained at a substantially reduced moisture content with respect to the exterior of the enclosure, because the adsorbent media removes moisture from the interior of the enclosure. The enclosure in which the filter element is placed includes an enclosure containing an electronic circuit or device, wherein the electronic circuit or device includes, without limitation, an organic light emitting diode, a hard drive, a display, or some combination thereof. For example, the filter element of the invention can be used as a moisture-absorbing flexible display for an electronic device. The flexible display comprises a lighted display (including displays formed using light emitting diodes) combined with the filter element, which absorbs moisture from the environment or enclosure in which the flexible display is used.

Depending on the amount of performance necessary, this media could be used in various applications and in various forms including particle filtration and chemical filtration in the same layer or confined space, combination particle filter and chemical filter for use in a gas turbine application, chemical filter as the only option for gas turbine systems, high flow applications in the semiconductor industry for fan assemblies, point of use, and full filter fabrication locations or labs, applications that require a "gettering" type filter, point of use filtration for semiconductor within clean rooms with minimal space and maximum efficiency, tool mount filter for semiconductor applications within clean rooms with minimal space and maximum efficiency, high flow applications in ceiling grids for clean rooms applications, applications that require a reduced weight but similar efficiencies, applications that require a reduced pressure drop but similar efficiencies, locations requiring low particle shedding, or layers of chemical filters can be used. Respirators, dust masks, surgical masks and gowns, surgical drapes, HEPA replacement including filters for semiconductor processing equipment and clean rooms, sir filtration for gasoline, natural gas or diesel powered engine, inlet filtration for air compressors, inlet filtration for dust collection equipment, vacuum cleaner filters, acid gas removal from air, cartridges for dryers, CBRN protection materials, wound care, HVAC applications, cabin air filtration, room air cleaner, fuel filter, lube filter, oil filters, liquid filters, air filter for fuel cell application, process filters, insulation material, filters for disk drives, filters for electronics enclosures, chromatographic separations, bio-separations can all be made with the materials of the application.

By alternately stacking flat sheet chemical filtration with a spacing media, this can create flow channels within the element. These channels allow the gas fluid to be filtered to pass across the media in such a manner as to perform the desired reactions, while, at the same time, maintaining a lower pressure drop than the chemical filtration media would allow by itself. The spacing media may be chemically treated to assist in filtration or may be inert.

Figure 3:
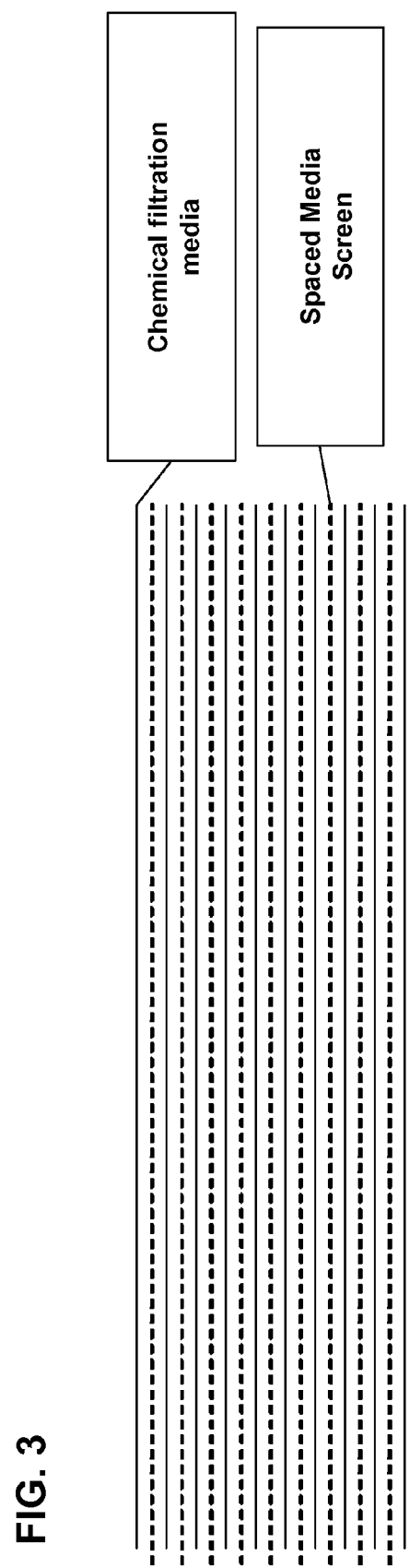
FIG. 3 is a cross section of an assembly of the structures of the invention. The assembly comprises a chemical filtration media and a spacer layer. The chemical filtration media comprises a nanofiber layer with the dispersed active particulate within the nanofiber layer. The spacer media is a layer that provides sufficient open volume within the structure to ensure that fluid can flow with little impediment through the structure.

Similarly, flow channels in a filter element can be created by co-rolling the spacing media and chemical filtration media around a chemically active or inert core. This can be seen in the (FIG. 3).

Once the fine fiber layer containing the active or active inert particulate of the invention is prepared, the layer must be mechanically assembled into a useful active or adsorbent or absorbent structure. Nanofiber layers are typically spun onto a substrate material which can be a scrim, a cellulosic substrate, a mixed synthetic cellulosic substrate or a purely cellulosic substrate. The nanofiber layers containing the active or inert particulate are electrospun onto said substrates and the substrate can then be rolled into an absorbent structure. Alternatively, the layer can be cut into similar portions and stacked to form an absorbent layer. It is important that the internal structure of any assembly of the nanofiber layers has sufficient air flow to ensure that the air can pass easily through the assembly. In this case, the assembly would act, not as a filter, but purely as an absorbent assembly structure. In an alternative structure, the layers of fine fiber and reactive or active particulate can be assembled into a structure that filters and reacts, adsorbs, or absorbs. Such varying structures have applications in a variety of end uses. The former structure has little or no filtration properties and can remove reactive contaminant materials from fluid streams such as air streams or liquid streams simply using a flow-through mechanism. The latter structure can remove particulate, and can remove chemical species from a fluid such as air, simultaneously with the filtration operations.

In certain preferred arrangements of the wound or stacked layers of the invention, the media can be configured for a straight through flow either in a flow without filtration properties or a flow including passage through a filter layer. In such a fluid flow, the fluid will enter in one direction through a first flow face and exit moving in the same direction from a second flow face. Within the filter structure, the fluid may not interact with a surface that acts as a filter or it may interact with a flow, may contact a surface that obtains filtration properties. Generally, one preferred filter construction is a wound construction including a layer of media that is turned repeatedly about a center point forming a coil such that the filter media will be rolled, wound or coiled. One preferred useful structure is a corrugated structure in which the material has a fluted construction. Such flutes can be formed and combined with a face sheet. Once the corrugated media is combined with the uncorrugated media in the form of a face sheet, the resulting structure can be coiled and formed into a useful assembly. When using this type of media construction, the flutes form alternating peaks and troughs in the corrugated structure. In certain constructions, the upper flutes form flute chambers which can be closed at a downstream and while the flute chambers have upstream ends that are closed to form other rows of flutes. In such a structure, the opened and closed areas cause the fluid to pass through at least one corrugated wall to obtain filtration properties from the corrugated layer. In use, such corrugated media in a coiled assembly provides an intake area for a fluid stream such as air. Air enters a flute chamber in an open upstream end, the unfiltered fluid flow is not permitted to pass through a closed down stream end but is forced to proceed through a corrugated layer or fluted sheet to contact either the fiber of the corrugated layer or the active particulate to either filter particulate from the fluid stream, or to ensure that the material dispersed or dissolved in the fluid stream is reacted with, absorbed, or adsorbed onto the active particulate.

Experiment for Breakthrough Bench System

Figure 5:
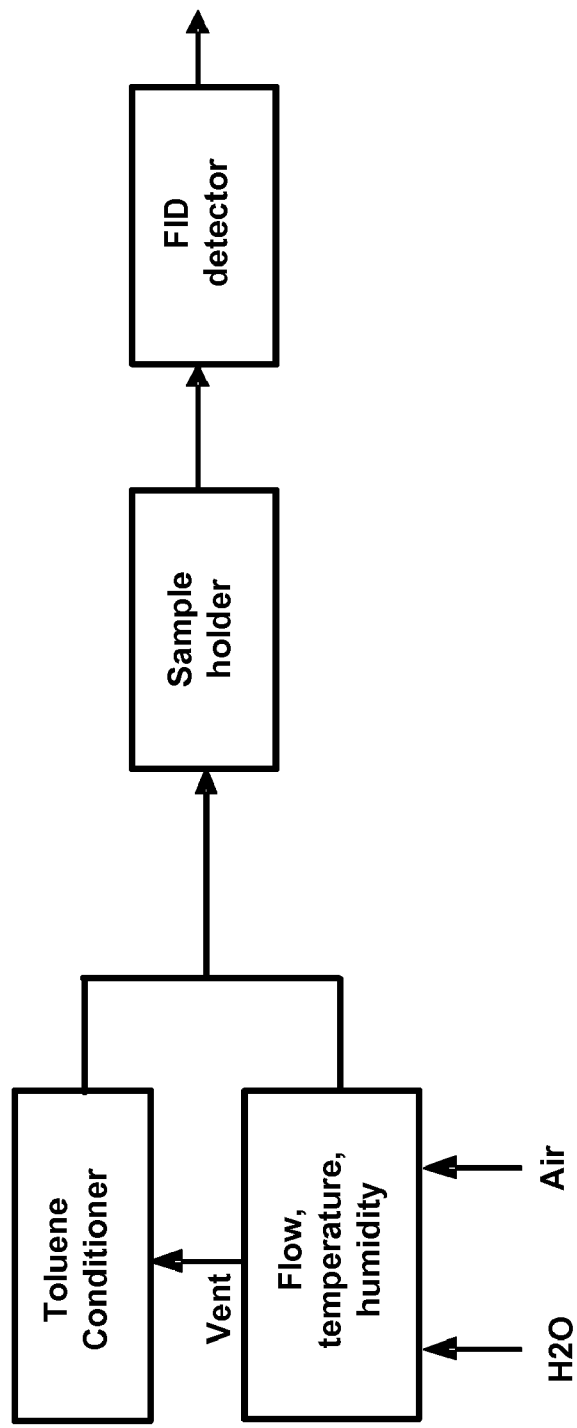
FIGS. 5 and 6 are a test apparatus and test results for the removal of a toluene test contaminant in air using a element of the invention.

Organic gas breakthrough tests were performed on all elements with contaminate of toluene at 50 ppm. A general block diagram of our breakthrough test bench design is given in FIG. 5. Breakthrough tests with a residence time of 0.12 sec were carried out to test adsorbent toluene capacities. The carbon media of the examples was conditioned inside the column (1.5 inch ID) until the relative humidity reached 50% and temperature arrived at 25° C. Then the air containing toluene (generated from a solvent generation system) flowed through the sample bed with a flow rate of 30 Lpm to begin the breakthrough test.

Figure 6:
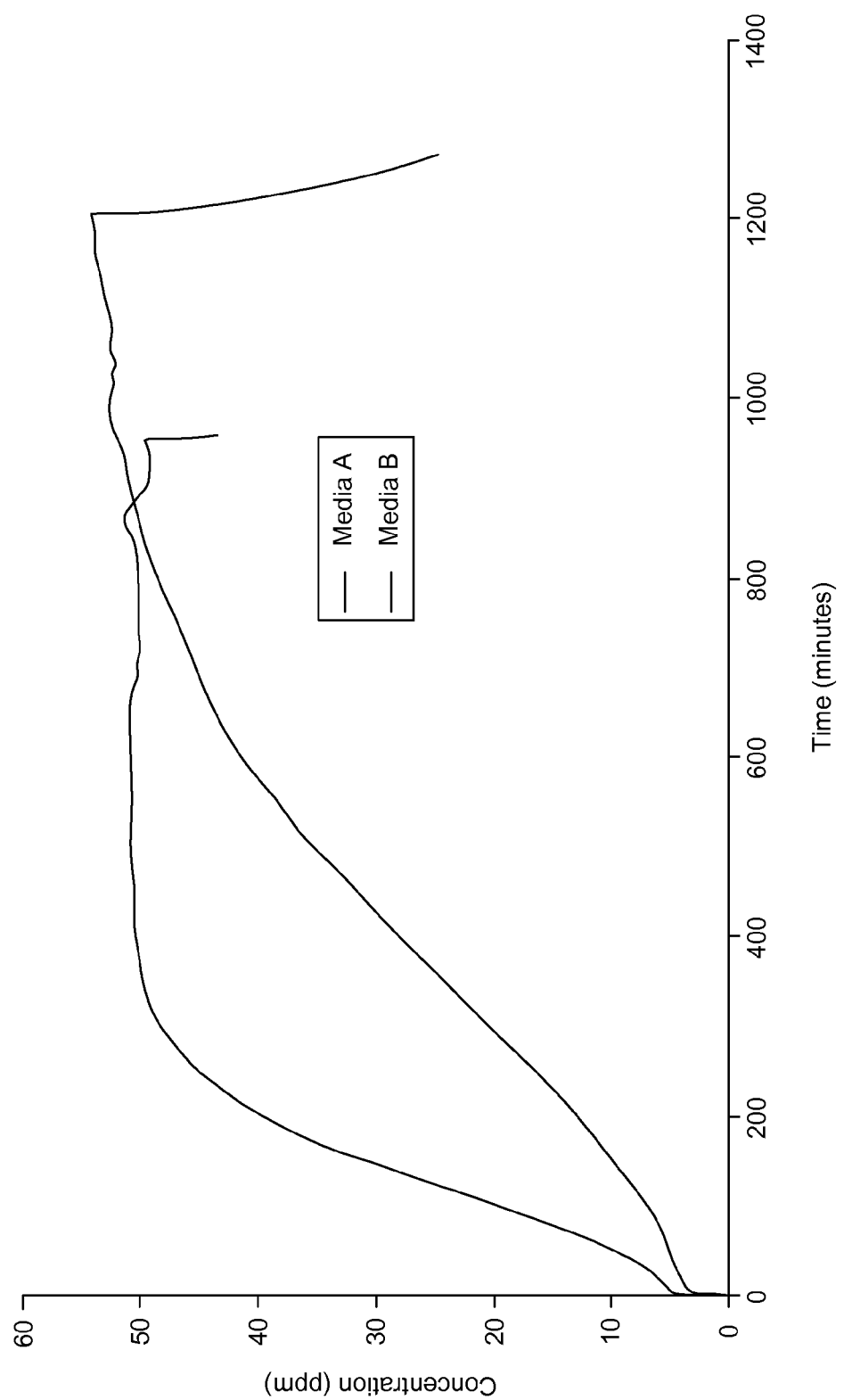

Contaminants were generated from certified gas standards delivered into the test air stream through mass flow controllers (Aalborg; Orangeburg, N.Y.; or Brooks/Emerson Process Management, Hatfield, Pa.). The relative humidity was controlled using a Flow-Temperature-Humidity Controller (Miller-Nelson Research, Inc.; Monterey, Calif.); Model HCS-401. A relative humidity of 50% RH was used for the studies presented herein. The temperature and relative humidity of the air stream upstream and downstream of the adsorbent bed were measured using calibrated temperature and humidity sensors (Vaisala; Woburn, Mass.; Model HMP233). The temperature of the adsorbent bed was controlled at 25° C. using a water-jacketed sample holder and a water bath. Detection of the upstream and downstream contaminant concentration was monitored using a JUM Flame Ionization Detector (FID). FIG. 6 is a breakthrough curves for all fine fiber entrapment elements tested. Non-impregnated and impregnated activated carbons have excellent removal efficiency and life for certain organic gases.

Since particle and fiber deposition are independent from each other, we can generate composites that have varying ratios of particles to fibers. We've generated composites that had nanofiber loading of 8-15% wt in the past, although no theoretical limit exists on these amounts. Consequently, on such structures, activated carbon loading was in 92-85% wt range.

Typically, the process involves deposition of a very light layer of nanofibers on a scrim for handling and integrity purposes, followed by the application of nanofiber/activated carbon composite, which constitutes the bulk of the overall composite. In the final stage, another layer of nanofiber-only layer is deposited to the top of the composite. This nanofiber only layer on the top and bottom surfaces help keep particle shedding to almost none, as we have not seen evidence of that in the past. They also help boost the particulate efficiency of the composite. The structure of the invention includes, a Nanofiber layer, a Nanofiber/carbon composite layer, a Nanofiber-only layer, and a Scrim.

Particulate efficiency is one of the key parameters that bring an edge-formed for this type of media. Below are particulate efficiency data for two nanofiber/activated carbon composites, with the difference being their basis weights. Measurements are recorded using TSI 3160 Automated Filter Tester, operated using DOP particles of varying size at 10.5 ft/min face velocity on flat sheet samples.

capacity. In this case, these media were challenged against toluene. Results show that varying the degree of carbon loading affected the breakthrough time and overall capacity of these media as shown in FIG. 6. Note that these media were tested not in a pleated form but rather in a spirally-winded form and hence the curve should be taken into consideration only for what it is intended to be presented for, and not for an actual performance in a respirator application.

Since particle and fiber deposition are independent from each other, we can generate composites that have varying ratios of particles to fibers. We've generated composites that had nanofiber loading of 8-15% wt in the past, although no

|  | Media A | | | Media B | | |
|---|---|---|---|---|---|---|
| Particle Size D (um) | Efficiency % | Penetration % | Resistance mmH20 | Efficiency % | Penetration % | Resistance mmH20 |
| 0.02 | 99.12 | 0.88 | 7.77 | 99.99 | 0.01 | 25.13 |
| 0.03 | 98.28 | 1.72 | 7.77 | 99.99 | 0.01 | 25.18 |
| 0.04 | 97.04 | 2.96 | 7.77 | 99.98 | 0.02 | 25.17 |
| 0.05 | 93.80 | 6.20 | 7.77 | 99.90 | 0.10 | 25.20 |
| 0.06 | 92.45 | 7.55 | 7.78 | 99.87 | 0.13 | 25.20 |
| 0.07 | 91.16 | 8.84 | 7.80 | 99.83 | 0.17 | 25.21 |
| 0.08 | 90.09 | 9.91 | 7.78 | 99.79 | 0.21 | 25.22 |
| 0.09 | 89.14 | 10.86 | 7.78 | 99.78 | 0.25 | 25.24 |
| 0.10 | 87.94 | 12.06 | 7.78 | 99.67 | 0.33 | 25.27 |
| 0.20 | 86.65 | 13.35 | 7.81 | 99.64 | 0.36 | 25.24 |
| 0.30 | 89.09 | 10.91 | 7.79 | 99.82 | 0.18 | 25.28 |
| 0.40 | 91.76 | 8.24 | 7.80 | 99.93 | 0.07 | 25.28 |
| Carbon loading | g/m2 | 26.38 | | g/m2 | 77.48 | |
| Carbon concentration | % | 85.52 | | % | 84.63 | |
| Total carbon + fiber | g/m2 | 30.85 | | g/m2 | 91.55 | |

This table shows particulate efficiencies of two nanofiber composites with different thicknesses. As one can see from the table above, by varying the composite thickness we have successfully changed the particulate efficiency of the composite. It is also possible to modify the particulate efficiency by varying the amount of nanofiber layer on the top and bottom surfaces of the composite without affecting the nanofiber/carbon composite in the middle. Furthermore, it is possible to introduce one or more nanofiber-only layer inside the middle composite in an attempt to boost the particulate efficiency to the desired target level. Another structure can include a Nanofiber layer, a Nanofiber/carbon composite layer, a Nanofiber-only layer and a Scrim.

This Nanofiber composite similar to that above, the difference is a nanofiber-only layer in the middle of the nanofiber-carbon composite functioning as a particulate efficiency enhancement stage. While particulate efficiency is one aspect unique to this invention, another aspect is chemical adsorption and removal of contaminants from gas phase. In an attempt to understand the effects of different levels of carbon loading, Media A and Media B, which were tested for particulate efficiency were also tested for chemical adsorption theoretical limit exists on these amounts. Consequently, on such structures, activated carbon loading was in 92-85% wt range.

Typically, the process involves deposition of a very light layer of nanofibers on a scrim for handling and integrity purposes, followed by the application of nanofiber/activated carbon composite, which constitutes the bulk of the overall composite. In the final stage, another layer of nanofiber-only layer is deposited to the top of the composite. This nanofiber only layer on the top and bottom surfaces help keep particle shedding to almost none, as we have not seen evidence of that in the past. They also help boost the particulate efficiency of the composite. The structure of the invention includes, a Nanofiber layer, a Nanofiber/carbon composite layer, a Nanofiber-only layer, and a Scrim.

Particulate efficiency is one of the key parameters that bring an edge-formed for this type of media. Below are particulate efficiency data for two nanofiber/activated carbon composites, with the difference being their basis weights. Measurements are recorded using TSI 3160 Automated Filter Tester, operated using DOP particles of varying size at 10.5 ft/min face velocity on flat sheet samples.

|  | Media A | | | Media B | | |
|---|---|---|---|---|---|---|
| Particle Size D (um) | Efficiency % | Penetration % | Resistance mmH20 | Efficiency % | Penetration % | Resistance mmH20 |
| 0.02 | 99.12 | 0.88 | 7.77 | 99.99 | 0.01 | 25.13 |
| 0.03 | 98.28 | 1.72 | 7.77 | 99.99 | 0.01 | 25.18 |

-continued

| Particle Size D (um) | Media A | | | Media B | | |
|---|---|---|---|---|---|---|
| | Efficiency % | Penetration % | Resistance mmH20 | Efficiency % | Penetration % | Resistance mmH20 |
| 0.04 | 97.04 | 2.96 | 7.77 | 99.98 | 0.02 | 25.17 |
| 0.05 | 93.80 | 6.20 | 7.77 | 99.90 | 0.10 | 25.20 |
| 0.06 | 92.45 | 7.55 | 7.78 | 99.87 | 0.13 | 25.20 |
| 0.07 | 91.16 | 8.84 | 7.80 | 99.83 | 0.17 | 25.21 |
| 0.08 | 90.09 | 9.91 | 7.78 | 99.79 | 0.21 | 25.22 |
| 0.09 | 89.14 | 10.86 | 7.78 | 99.78 | 0.25 | 25.24 |
| 0.10 | 87.94 | 12.06 | 7.78 | 99.67 | 0.33 | 25.27 |
| 0.20 | 86.65 | 13.35 | 7.81 | 99.64 | 0.36 | 25.24 |
| 0.30 | 89.09 | 10.91 | 7.79 | 99.82 | 0.18 | 25.28 |
| 0.40 | 91.76 | 8.24 | 7.80 | 99.93 | 0.07 | 25.28 |
| Carbon loading | g/m2 | 26.38 | | g/m2 | 77.48 | |
| Carbon concentration | % | 85.52 | | % | 84.63 | |
| Total carbon + fiber | g/m2 | 30.85 | | g/m2 | 91.55 | |

This table shows particulate efficiencies of two nanofiber composites with different thicknesses.

As one can see from the table above, by varying the composite thickness we have successfully changed the particulate efficiency of the composite. It is also possible to modify the particulate efficiency by varying the amount of nanofiber layer on the top and bottom surfaces of the composite without affecting the nanofiber/carbon composite in the middle. Furthermore, it is possible to introduce one or more nanofiber-only layer inside the middle composite in an attempt to boost the particulate efficiency to the desired target level. Another structure can include a Nanofiber layer, a Nanofiber/carbon composite layer, a Nanofiber-only layer and a Scrim.

This Nanofiber composite similar to that above, the difference is a nanofiber-only layer in the middle of the nanofiber-carbon composite functioning as a particulate efficiency enhancement stage. While particulate efficiency is one aspect unique to this invention, another aspect is chemical adsorption and removal of contaminants from gas phase. In an attempt to understand the effects of different levels of carbon loading, Media A and Media B, which were tested for particulate efficiency were also tested for chemical adsorption capacity. In this case, these media were challenged against toluene. Results show that varying the degree of carbon loading affected the breakthrough time and overall capacity of these media as shown in FIG. 6.

Note that these media were tested not in a pleated form but rather in a spirally-winded form and hence the curve should be taken into consideration only for what it is intended to be presented for, and not for an actual performance in a respirator application.

Figure 7:
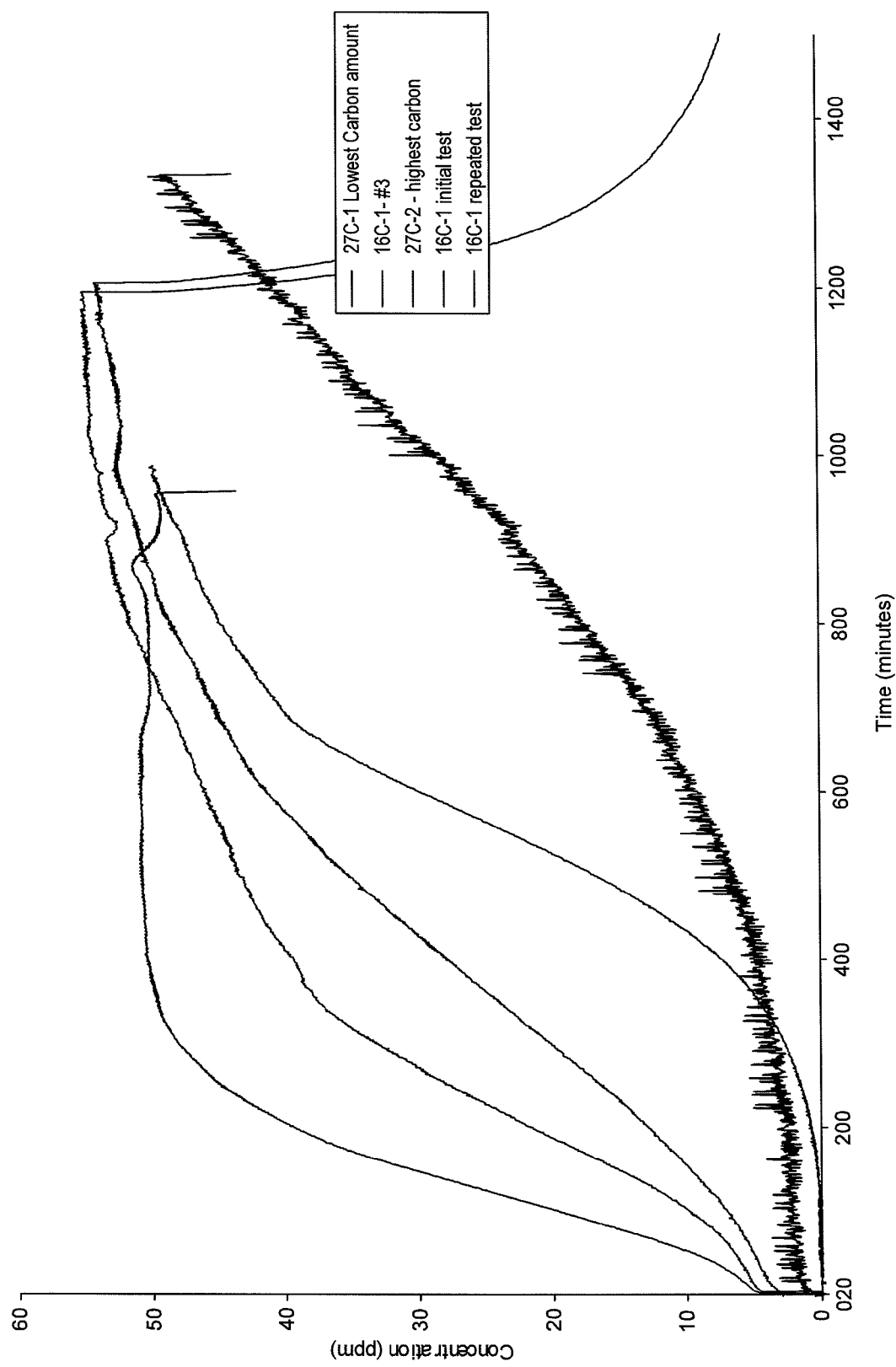
FIG. 7 shows the performance of a high surface area coconut shell carbon placed within the web of our fine fiber matrix in accelerated breakthrough test.

FIG. 7 shows the performance of a high surface area coconut shell carbon placed within the web of our fine fiber matrix in accelerated breakthrough test for toluene. Although the efficiency breakthrough curve for 50 ppm toluene for this material indicates it has some initial efficiency and life problems; we believe we can overcome this issue through increasing the overall length of the channel as well as new designs.

The above specification, examples and data provide a complete description of the manufacture and use of the composition of the invention. Since many embodiments of the invention can be made without departing from the spirit and scope of the invention, the invention resides in the claims hereinafter appended.

We claim:

1. An element comprising a filter media, the media comprising a web having first and second opposite flow faces; and a plurality of flutes; (i) each of said flutes having a first open end portion adjacent to said first flow face and a second open end portion adjacent to said second flow face; (ii) said media including a nonwoven substrate at least partially covered by a layer of fine fibers, said layer of fine fibers comprising a fine fiber layer and an active spacer particulate dispersed in a substantially uniform manner in the fiber layer, the particulate comprising 0.1 to 50 vol % of the layer, the fiber having a diameter of about 0.001 to about 5 microns, the layer having a thickness of 0.5 to 500 microns and a solidity of about 0.1 to 65%; wherein the element comprises a flow-by path such that a fluid can flow in a path parallel to the substrate; and wherein solidity of a fine fiber layer without the active spacer particulate is greater than the solidity of a fine fiber layer formed with the active spacer particulate.

2. The element of claim 1, wherein the layer of fine fiber is heat treated forming a porous membrane.

3. The element of claim 1, wherein selected ones of said flutes being open at said first end portion and closed at said second end portion; and selected ones of said flutes being closed at said first end portion and open at said second end portion provides a fluid path through the fluted layer.

4. The element of claim 1, wherein the fiber has a diameter of about 0.001 to 0.5 micron.

5. The element of claim 1, wherein the web has a figure of merit of 100 to 10,000.

6. The element of claim 1, wherein the thickness of the fiber web is about 1 to 100 times the fiber diameter.

7. The element of claim 1, wherein the web comprises about 5 to 95 wt % fiber and about 95 to 5 wt % active spacer particulate comprising both active and inert particulate.

8. The element of claim 1, wherein the web comprises about 30 to 75 wt % fiber and about 70 to 25 wt % active spacer particulate.

9. The element of claim 1, wherein the active spacer particulate has a major dimension less than about 5000 microns.

10. The element of claim 1, wherein the particulate has a major dimension of less than about 200 microns.

11. The element of claim 1, wherein the particulate has a major dimension of about 5 to 200 microns.

12. The element of claim 1, wherein the particulate has a major dimension of about 0.05 to 100 microns.

13. The element of claim 1, wherein the particulate has a major dimension of about 0.1 to 70 microns.

14. The element of claim 1, wherein the web has a Frazier permeability of about 1 to about 50 meters-minutes$^{-1}$ and an efficiency of about 40 to about 99.9999% under ASTM 1215-89 using monodispersed 0.78 micron polystyrene latex particulate at 6.1 m-min$^{-1}$ or 20 ft-min$^{-1}$.

15. The element of claim 1, wherein the filter structure comprises one or more layers of fine fiber having a thickness of at least about 0.5 micron, at least one layer is free of the particulate and at least one layer has particulate disbursed throughout the fine fiber layer.

16. The element of claim 1, wherein the particulate is an absorbent.

17. The element of claim 1, wherein the particulate is an adsorbent.

18. The element of claim 1, wherein the particulate is a combination of an inert particulate and the active spacer particulate.

19. The element of claim 1, wherein the particulate is substantially spherical.

20. The element of claim 1, wherein the particulate is amorphous.

21. The element of claim 1, wherein the particulate is monodispersed.

22. The element of claim 1, wherein the particulate is polydispersed.

23. The element of claim 1, wherein the web has a gradient in the distribution of the active spacer particulate.

24. The element of claim 1, wherein the web has a gradient in a distribution of an inert particulate spacer means.

25. The element of claim 1, wherein the web has a gradient in the distribution of the fiber.

26. The element of claim 1, wherein said media and said plurality of flutes form a frame construction and wherein said media and frame construction have a circular cross section.

27. The element of claim 1, further including a panel structure; said media being mounted within said panel structure with a support.

28. A method for filtering a fluid, the method comprising: (a) directing fluid through a filter medium having first and second opposite flow faces; and a plurality of flutes; the medium comprising; (i) each of the flutes having a first end portion adjacent to the first flow face and a second end portion adjacent to the second flow face; (ii) selected ones of the flutes being open at the first end portion and closed at the second end portion; and selected ones of the flutes being close at the first end portion and open at the second end portion; (iii) the medium including a nonwoven substrate at least partially covered by a layer of fine fibers; the layer of fine fibers comprising a fine fiber layer and an active spacer particulate dispersed in a substantially uniform manner in the fiber layer, the particulate comprising 0.1 to 50 vol % of the layer, the fiber having a diameter of about 0.001 to about 5 microns, the layer having a thickness of 0.5 to 500 microns and a solidity of about 0.1 to 65%; wherein the element comprises a flow-by path such that a fluid flows in a path parallel to the substrate; and wherein solidity of a fine fiber layer without the active spacer particulate is greater than the solidity of a fine fiber layer formed with the active spacer particulate.

* * * * *

UNITED STATES PATENT AND TRADEMARK OFFICE
CERTIFICATE OF CORRECTION

PATENT NO.        : 8,048,210 B2
APPLICATION NO.   : 12/648772
DATED             : November 1, 2011
INVENTOR(S)       : Dallas et al.

It is certified that error appears in the above-identified patent and that said Letters Patent is hereby corrected as shown below:

Title Page, (75) Inventors: Please change the second named inventor's name from "Lefei Ding" to --William Lefei Ding--.

Signed and Sealed this
Sixth Day of March, 2012

David J. Kappos
*Director of the United States Patent and Trademark Office*